United States Patent

Schmitt-Willich et al.

[11] Patent Number: 5,874,061
[45] Date of Patent: Feb. 23, 1999

[54] CASCADE POLYMER COMPLEXES, PROCESS FOR THEIR PRODUCTION AND PHARMACEUTICAL AGENTS CONTAINING SAID COMPLEXES

[75] Inventors: Heribert Schmitt-Willich; Johannes Platzek; Bernd Raduchel; Hanns-Joachim Weinmann; Wolfgang Ebert; Bernd Misselwitz, all of Berlin; Andreas Muhler, Neuenhagen; Thomas Frenzel, Berlin, all of Germany

[73] Assignee: Schering Aktiengesellschaft, Berlin, Germany

Related U.S. Application Data

[60] Provisional application No. 60/009,619 Jan. 5, 1996.

[21] Appl. No.: 777,666

[22] Filed: Dec. 20, 1996

[30] Foreign Application Priority Data

Dec. 22, 1995 [DE] Germany .................. 195 49 286.2

[51] Int. Cl.[6] ............. A61B 5/055; C07D 225/00; C08F 283/00; C07F 5/00
[52] U.S. Cl. .............. 424/9.363; 424/9.36; 424/9.364; 424/9.365; 424/1.65; 540/465; 540/473; 540/474; 525/417; 534/10; 534/14; 534/15; 534/16
[58] Field of Search .................. 424/9.36, 9.363, 424/9.364, 9.365, 1.65; 540/465, 473, 474; 564/191, 198; 525/417; 534/10, 14, 15, 16

[56] References Cited

U.S. PATENT DOCUMENTS 5,364,614 11/1994 Platzek et al. ................ 424/9.3
5,527,524 6/1996 Tomalia et al. ................ 424/1.33

FOREIGN PATENT DOCUMENTS 2179624 6/1995 Canada.
2181070 9/1995 Canada.
2187921 11/1995 Canada.
2194560 1/1996 Canada.

OTHER PUBLICATIONS

"Dendrimer-based Metal Chelates: A New Class of Magnetic Resonance Imaging Contrast Agents," Magnetic Resonance in Medicine, 31(1):1–8, Jan. 1, 1994, Wiener et al.

Primary Examiner—José G. Dees
Assistant Examiner—Michael G. Hartley
Attorney, Agent, or Firm—Millen, White, Zelano, & Branigan, P.C.

[57] ABSTRACT

Cascade polymer complexes that contain
a) complexing ligands of general formula I $$A-\{X-[Y-(Z-(W-K_w)_z)_y]_x\}_a, \quad (I)$$

in which
A stands for a nitrogen-containing cascade nucleus of base multiplicity a,
X and Y, independently of one another, stand for a direct bond or a cascade reproduction unit of reproduction multiplicity x or y,
Z and W, independently of one another, stand for a cascade reproduction unit of reproduction multiplicity z or w,
K stands for the radical of a complexing agent, a stands for numbers 2 to 12, x, y, z and w, independently of one another, stand for numbers 1 to 4,
provided that at least two reproduction units are different, that $16 \leq a \cdot x \cdot y \cdot z \cdot w \leq 64$ holds true for the product of the multiplicities, and that at least one of cascade reproduction units X, Y, Z, W stands for a 1,4,7,10-tetraazacyclododecane or 1,4,8,11-tetraazacyclotetradecane reproduction unit,
b) at least 16 ions of an element of atomic numbers 20 to 29, 39, 42, 44 or 57–83,
c) optionally cations of inorganic and/or organic bases, amino acids or amino acid amides as well as
d) optionally acylated terminal amino groups are valuable compounds for diagnosis and therapy.

13 Claims, 1 Drawing Sheet

CASCADE POLYMER COMPLEXES, PROCESS FOR THEIR PRODUCTION AND PHARMACEUTICAL AGENTS CONTAINING SAID COMPLEXES

This application claims the benefit of U.S. provisional application No. 60/009,619, filed Jan. 5, 1996.

The invention relates to the object characterized in the claims, i.e., new cascade polymer complexes, agents that contain these compounds, the use of the complexes in diagnosis and therapy, and a process for the production of these compounds and agents.

The contrast media that are now used in clinical practice for the modern imaging processes of nuclear spin tomography (MRI [magnetic resonance imaging]) and computer tomography (CT) [Magnevist$^{(R)}$, Pro Hance$^{(R)}$, Ultravist$^{(R)}$ and Omniscan$^{(R)}$ are dispersed in the entire extracellular space of the body (intravascular space and interstitium). This distribution space comprises about 20% of the volume of the body.

In clinical practice, extracellular MRI contrast media were first used successfully in the diagnosis of cerebral and spinal disease processes since here a quite special situation exists with respect to the regional distribution space. In the brain and spinal cord, extracellular contrast media in healthy tissue do not leave the intravascular space because of the blood-brain barrier. In the case of pathological processes with disruption of the blood-brain barrier (e.g., malignant tumors, inflammations, demyelinating diseases, etc.), regions with elevated blood-vessel permeability then develop inside the brain for these extracellular contrast media (Schmiedl et al., MRI of blood-brain barrier permeability in astrocytic gliomas: application of small and large molecular weight contrast media, Magn. Reson. Med. 22: 288, 1991). Affected tissue can be identified with high contrast relative to healthy tissue by exploiting this disruption of vascular permeability.

Outside of the brain and the spinal cord, however, no such permeability barrier exists for the above-mentioned contrast media (Canty et al., First-pass entry of nonionic contrast agent into the myocardial extravascular space. Effects on radiographic estimate of transit time and blood volume. Circulation 84: 2071, 1991). Thus, the concentration of the contrast medium is no longer dependent on vascular permeability, but only on the size of the extracellular space in the corresponding tissue. Delimitation of the vessels relative to the surrounding interstitial space using this contrast medium is not possible.

A contrast medium that is dispersed exclusively in the vascular space would be desirable, particularly for the visualization of vessels. The purpose of such a blood-pool agent is to make it possible, with the aid of nuclear spin tomography, to delimit tissue with sufficient blood supply from tissue with insufficient blood supply, and thus to diagnose an ischemia. Infarcted tissue can also be delimited, based on its anemia, from surrounding healthy or ischemic tissue if a vasal contrast medium is used. This is of special importance if the point is to distinguish a myocardial infarction from an ischemia.

To date, most of the patients in whom there is suspicion of cardiovascular disease (this disease is the most frequent cause of death in Western industrialized countries) have to undergo invasive diagnostic tests. In angiography at present, diagnostic radiology with the aid of iodine-containing contrast media is used in particular. These tests suffer from various drawbacks: they are associated with the risk of radiation exposure, as well as with difficulties and stresses, which therefore particularly have the effect that the iodine-containing contrast media, as compared with NMR contrast media, have to be used in much higher concentrations.

There is therefore a need for NMR contrast media which can mark the vascular space (blood-pool agents). These compounds are to be distinguished by good compatibility and by high effectiveness (high increase of signal intensity with MRI)

Thus far, the attempt to solve at least a part of this problem by using complexing agents that are bound to macromolecules or biomolecules has been successful only to a limited extent.

Thus, for example, the number of paramagnetic centers in the complexes that are described in European Patent Applications No. 0 088 695 and No. 0 150 844 is not sufficient for satisfactory imaging.

If the number of metal ions required is increased by repeated introduction of complexing units into a macromolecular biomolecule, this is associated with an intolerable impairment of the affinity and/or specificity of this biomolecule [J. Nucl. Med. 24, 1158 (1983)).

Macromolecules can generally be suitable as contrast media for angiography. But 24 hours after intravenous injection in rats, albumin-GdDTPA (Radiology 1987; 162: 205), e.g., shows a concentration in the liver tissue that constitutes almost 30% of the dose. In addition, only 20% of the dose is eliminated in 24 hours.

The macromolecule polylysine-GdDTPA (European Patent Application, Publication No. 0 233 619) has also proved suitable as blood-pool agent. Because of production, however, this compound consists of a mixture of molecules of different sizes. In excretion tests in rats, it was shown that this macromolecule is excreted unchanged by glomerular filtration through the kidneys. Due to factors related to synthesis, however, polylysine-GdDTPA may also contain macromolecules that are so large that they cannot pass through the capillaries of the kidneys in the case of glomerular filtration and thus remain in the body.

Also, macromolecular contrast media based on carbohydrates, e.g., dextran, have been described (European Patent Application, Publication No. 0 326 226). The drawback of these compounds lies in the fact that the latter generally carry only about 5% of the signal-enhancing paramagnetic cation.

The polymers described in European Patent Application No. 0 430 863 already represent a step toward blood-pool agents since they no longer exhibit the size and molecular weight relative to heterogeneity that are characteristic of the previously mentioned polymers. They leave something to be desired, however, as regards complete elimination, compatibility, and/or effectiveness.

The object was therefore to make available new diagnostic tools particularly to identify and locate vascular diseases that do not have the above-mentioned drawbacks. This object is achieved by this invention.

It has been found that complexes which consist of nitrogen-containing cascade polymers and which are provided with complexing ligands, at least 16 ions of an element of atomic numbers 20–29, 39, 42, 44 or 57–83, and optionally cations of inorganic and/or organic bases, amino acids or amino acid amides, are surprisingly very well suited for the production of NMR [nuclear magnetic resonance] and x-ray diagnostic agents without exhibiting the mentioned drawbacks.

The complexing cascade polymers according to the invention can be described by general formula I

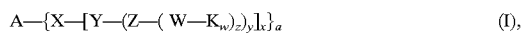  (I), in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, K stands for the radical of a complexing agent, a stands for numbers 2 to 12, x, y, z and w, independently of one another, stand for numbers 1 to 4, provided that at least two reproduction units are different, that $16 \leq a \cdot x \cdot y \cdot z \cdot w \leq 64$ holds true for the product of the multiplicities, and that at least one of cascade reproduction units X, Y, Z, W stands for a 1,4,7,10-tetraazacyclododecane or 1,4,8,11-tetraazacyclotetradecane reproduction unit. As cascade nucleus A, the following are suitable: nitrogen atom,

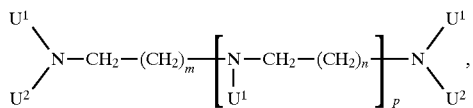

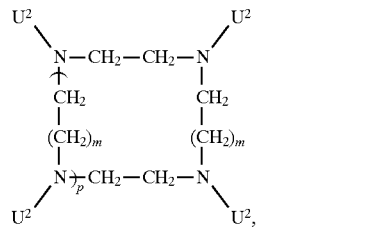

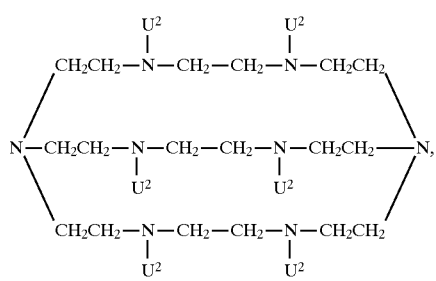

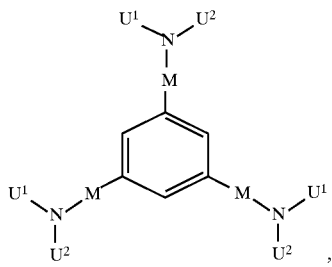

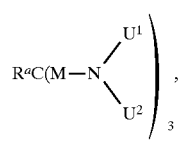

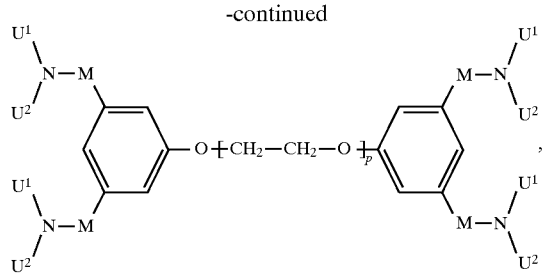

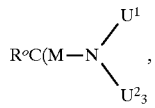

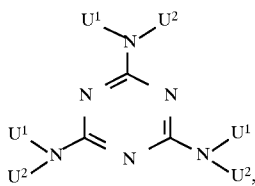

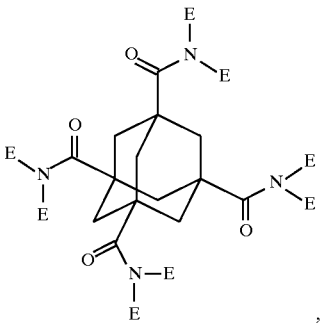

in which
m and n stand for numbers 1 to 10,
p stands for numbers 0 to 10,
$U^1$ stands for $Q^1$ or E,
$U^2$ stands for $Q^2$ or E with
E meaning the group

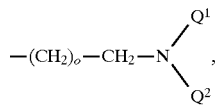

in which
stands for numbers 1 to 6,
$Q^1$ stands for a hydrogen atom or $Q^2$ and
$Q^2$ stands for a direct bond
M stands for a $C_1-C_{10}$ alkylene chain which optionally is interrupted by 1 to 3 oxygen atoms and/or optionally is substituted with 1 to 2 oxo groups,
$R^o$ stands for a branched or unbranched $C_1-C_{10}$ alkyl radical, a nitro, amino, carboxylic acid group or for

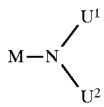

in which number $Q^2$ corresponds to base multiplicity a.

The nitrogen atom, whose three bonds (base multiplicity a=3) in a first "inner layer" (generation 1) are occupied by three reproduction units X or Y (if X stands for a direct bond) or Z (if X and Y in each case stand for a direct bond), represents the simplest case of a cascade nucleus; in other words: the three hydrogen atoms of the basic cascade starter ammonia $A(H)_a = NH_3$ have been substituted by three reproduction units X or Y or Z. In this case, number $Q^2$ contained in cascade nucleus A represents base multiplicity a.

Reproduction units X, Y, Z and W contain —$NQ^1Q^2$ groups, in which $Q^1$ means a hydrogen atom or $Q^2$ and $Q^2$ means a direct bond. The number $Q^2$ contained in the respective reproduction unit (e.g., X) corresponds to the reproduction multiplicity of this unit (e.g., x in the case of X). The product of all multiplicities $a \cdot x \cdot y \cdot z \cdot w$ indicates the number of complexing agent radicals K bound in the cascade polymers. The polymers according to the invention contain at least 16 and at most 64 radicals K in the molecule, which in each case can bond one to a maximum of three (in the case of divalent ions), preferably one ion, to an element of the above-mentioned atomic numbers.

The last generation, i.e., reproduction unit W bound to complexing agent radical K, is bound to K with NH groups (—$NQ^2Q^2$ with $Q^1$ meaning a hydrogen atom and $Q^2$=direct bond), while the preceding reproduction units can be linked together both by $NHQ^2$ groups (e.g., by acylation reactions) and by $NQ^2Q^2$ groups (e.g., by alkylation reactions).

The cascade polymer complexes according to the invention exhibit a maximum of 10 generations (i.e., more than just one of reproduction units X, Y and Z can also be present in the molecule in each case), but preferably 2 to 4 generations, in which at least two of the reproduction units in the molecule are different.

As preferred cascade nuclei A, those are indicated which fall under the above-mentioned general formulas if m stands for numbers 1–3, especially preferably for number 1, n stands for numbers 1–3, especially preferably for number 1, p stands for numbers 0–3, especially preferably for numbers 1 and 3, O stands for numbers 1–2, especially preferably for number 7, M stands for a —$CH_2$, —CO or —$CH_2CO$ group and $R^o$ stands for a —$CH_2NU^1U^2$, $CH_3$ or $NO_2$ group.

Preferred are furthermore cascade nuclei A which fall under the second and fourth formulae of the eight general formulae given above, especially under general formula

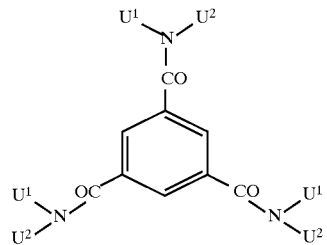

in which $U^1$ and $U^2$ stand for the group E with o meaning the numbers 1 or 2.

As further preferred cascade starters $A(H)_a$, there can be listed, e.g.:

(In the parentheses, base multiplicity a is indicated for the case where subsequent mono- or disubstitution is used in building the next generation)

| | |
|---|---|
| Tris(aminoethyl)amine | (a = 6 or 3); |
| tris(aminopropyl)amine | (a = 6 or 3); |
| diethylenetriamine | (a = 5 or 3); |
| triethylenetetramine | (a = 6 or 4); |
| tetraethylenepentamine | (a = 7 or 5); |
| 1,3,5-tris(aminomethyl)benzene | (a = 6 or 3); |
| trimesic acid triamide | (a = 6 or 3); |
| 1,4,7-triazacyclononane | (a = 3); |
| 1,4,7,10-tetraazacyclododecane | (a = 4); |
| 1,4,7,10,13-pentaazacyclopentadecane | (a = 5); |
| 1,4,8,11-tetraazacyclotetradecane | (a = 4); |
| 1,4,7,10,13,16-hexaazacyclooctadecane | (a = 6); |
| 1,4,7,10,13,16,19,22,25,28-decaazacyclotriacontane | (a = 10); |
| tetrakis(aminomethyl)methane | (a = 8 or 4); |
| 1,1,1-tris(aminomethyl)ethane | (a = 6 or 3); |
| tris(aminopropyl)-nitromethane | (a = 6 or 3); |
| 2,4,6-triamino-1,3,5-triazine | (a = 6 or 3); |
| 1,3,5,7-adamantanetetracarboxylic acid amide | (a = 8 or 4); |
| 3,3',5,5'-diphenylether-tetracarboxylic acid amide | (a = 8 or 4); |
| 1,2-bis[phenoxyethane]-3',3",5',5"-tetracarboxylic acid amide | (a = 8 or 4); |
| 1,4,7,10,13,16,21,24-octaazabicyclo[8.8.8]hexacosan | (a = 6). |

It can be pointed out that the definition as cascade nucleus A and thus the separation of cascade nucleus and first reproduction unit can be selected by purely formal means and thus independently of the actual synthesis of the desired cascade polymer complexes. Thus, e.g., the tris(aminoethyl) amine used in Example 4 can be considered as cascade nucleus A itself (compare the general formula, indicated first for A, with m=n=p=1, $U^1$=E with o meaning number 1 and $U^1=U^2=Q^2$) but also as a nitrogen atom (=cascade nucleus A), which as a first generation exhibits three reproduction units

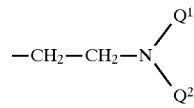

(compare the definition of E).

Cascade reproduction units X, Y, Z and W are determined, independently of one another, by

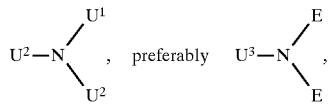

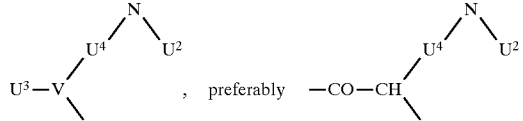

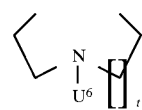 with t meaning numbers 1 or 2,

-continued

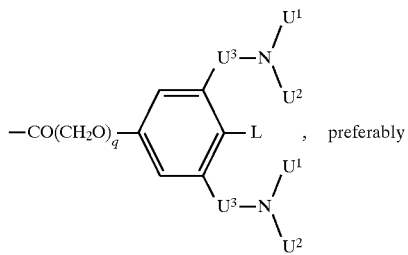, preferably

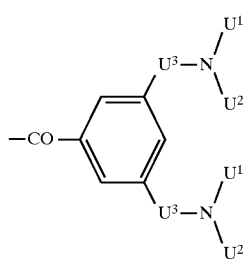

in which
U¹ stands for Q¹ or E,
U² stands for Q² or E with E meaning the group

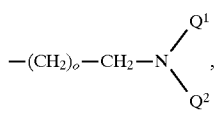

in which
o stands for numbers 1 to 6, preferably 1 to 2, preferably 1 to 2
Q¹ stands for a hydrogen atom or Q²,
Q² stands for a direct bond,
U³ stands for an —NHCO— $(CH_2)_o$ chain or a $C_1$–$C_{20}$, preferably $C_1$–$C_{10}$, alkylene chain, which optionally is interrupted by 1 to 10, preferably 1 to 2 oxygen atoms and/or 1 to 2 —N(CO)$_q$—R² radicals, 1 to 2 phenylene and/or 1 to 2 phenylenoxy radicals and/or optionally is substituted by 1 to 2 oxo, thioxo, carboxy, $C_1$–$C_5$ alkylcarboxy, $C_1$–$C_5$ alkoxy, hydroxy, $C_1$–$C_5$ alkyl groups,
in which
q stands for numbers 0 or 1 and
R² stands for a hydrogen atom, a methyl or an ethyl radical, which optionally is substituted with 1–2 hydroxy or 1 carboxy group(s),
L stands for a hydrogen atom or the group

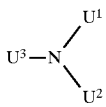

V stands for methine group

if at the same time U⁴ means a direct bond or group M and U⁵ has one of the meanings of U³ or V stands for group

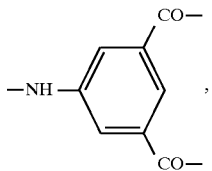, if at the same time U⁴ and U⁵ are identical and mean the direct bond or group M,
U⁵' stands for the group M, and
U⁶ stands for group

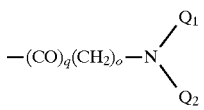

or a direct bond provided that at least one of the cascade reproduction units stands for the above-indicated 1,4,7,10-tetraazacyclododecane or 1,4,8,11-tetraazacyclotetradecane reproduction unit; preferred is the 1,4,7,10-tetraazacyclododecane reproduction unit. Preferred cascade reproduction units X, Y, Z and W are those
in which in the above-mentioned general formulas, radical U³ stands for —CO—, —COCH₂OCH₂CO—, —COCH₂—, —CH₂CH₂—, —CONHC₆H₄—, —NHCOCH₂—, —COCH₂CH₂CO—, —COCH₂CH₂CH₂CH₂CO—, —COCH₂CH₂CH₂CH₂CO—, —CONHCH₂CH₂NHCOCH₂CH₂CO—, —COCH₂CH₂NHCOCH₂CH₂CO—, radical U⁴ stands for a direct bond, for —CH₂CO—, radical U⁵ stands for a direct bond, for —(CH₂)₄—, —CH₂CO—, —CH(COOH)—, CH₂OCH₂CH₂—, —CH₂C₆H₄—, CH₂—C₆H₄OCH₂CH₂—, radical E stands for a group

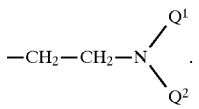

The following can be cited as examples of cascade reproduction units X, Y, Z and W:
—CH₂CH₂NH—; —CH₂CH₂N<;
—COCH(NH—)(CH₂)₄NH—; —COCH(N<)(CH₂)₄N<;
—COCH₂OCH₂CON(CH₂CH₂NH—)₂;
—COCH₂OCH₂CON(CH₂CH₂N<)₂;
—COCH₂N(CH₂CH₂NH—)₂; —COCH₂N(CH₂CH₂N<)₂;
—COCH₂NH—; —COCH₂N<;
—COCH₂CH₂CON(CH₂CH₂NH—)₂;
—COCHCH₂CH₂CON(CH₂CH₂N<)₂;
—COCH₂OCH₂CONH—C₆H₄—CH[CH₂CON(CH₂CH₂NH—)₂]₂;
—COCH₂OCH₂CONH—C₆H₄—CH[CH₂CON(CH₂CH₂N<)₂]₂;
—COCH₂CH₂CO—NH—C₆H₄—CH[CH₂CON(CH₂CH₂NH—)₂]₂;
—COCH₂CH₂CO—NH—C₆H₄—CH[CH₂CON(CH₂CH₂N<)₂]₂;
—CONH—C₆H₄—CH[CH₂CON(CH₂CH₂NH—)₂]₂;
—CONH—C₆H₄—CH[CH₂CON(CH₂CH₂N<)₂]₂;
—COCH(NH—)CH(COOH)NH—; —COCH(N<)CH(COOH)N<;

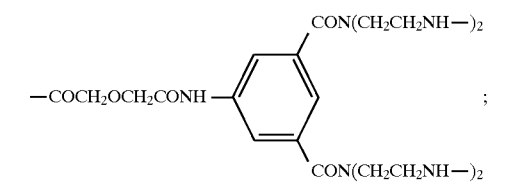;
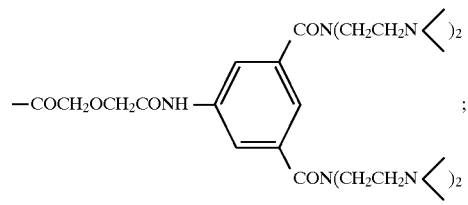;
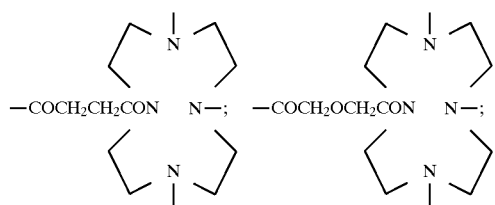
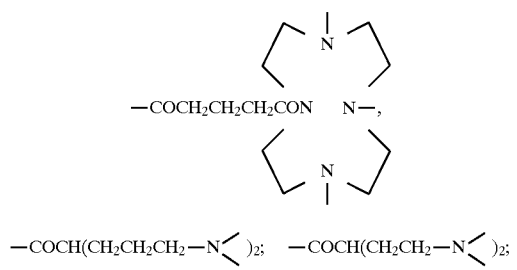;
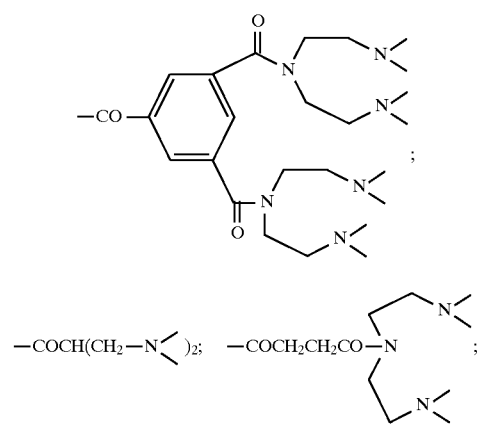
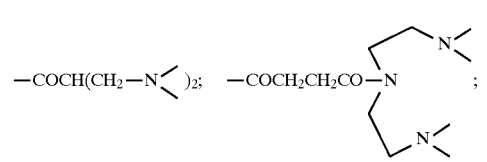
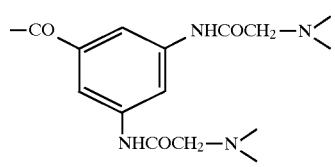
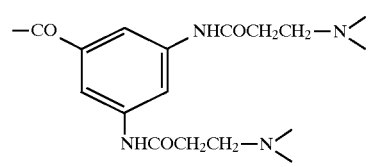
-continued
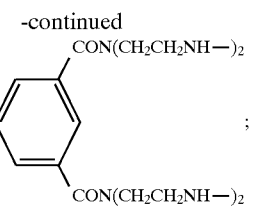;
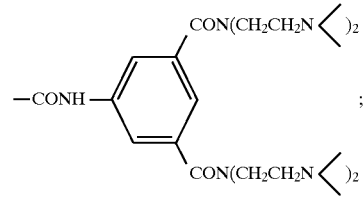;
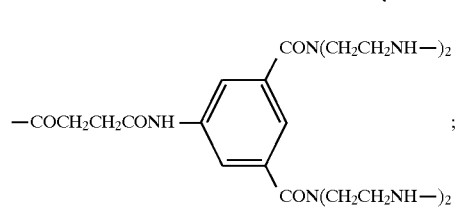;
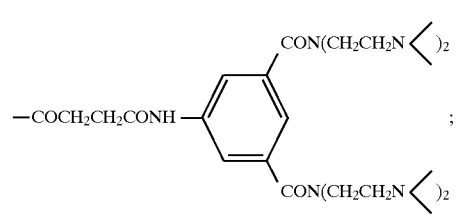;
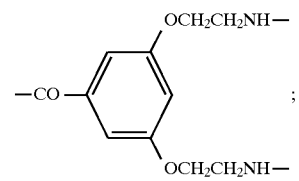;
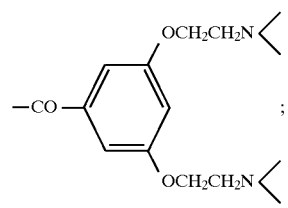;
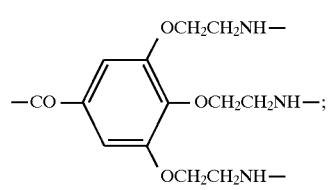;
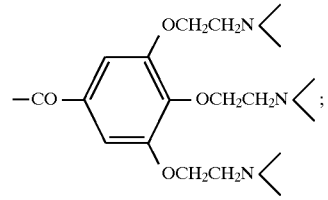;

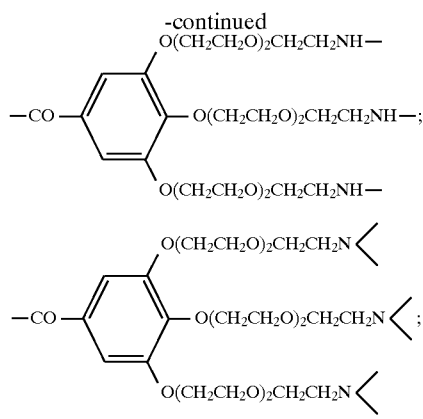

Complexing agent radicals K are described by general formulas IA, IB and IC:

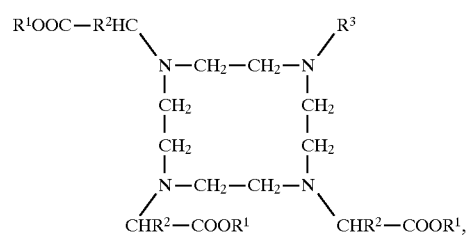

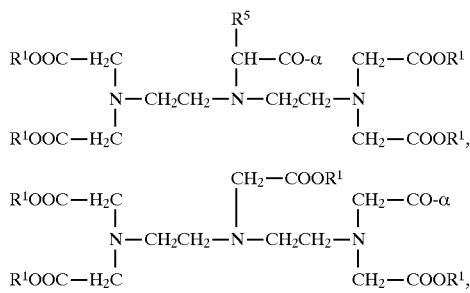

in which
R$^1$, independently of one another, stand for a hydrogen atom or a metal ion equivalent of atomic numbers 20–29, 39, 42–44 or 57–83, R$^2$ stands for a hydrogen atom, a methyl or an ethyl radical which optionally is substituted with 1–2 hydroxy or 1 carboxy group(s), R$^3$ stands for a

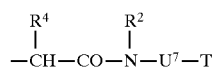

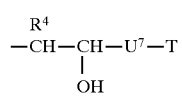

R$^4$ stands for a hydrogen atom or a straight-chain, branched, saturated or unsaturated C$_1$–C$_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s), R$^5$ stands for a hydrogen atom or for R4, U$^7$ stands for a straight-chain, branched, saturated or unsaturated C$_1$–C$_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), and the phenylene groups that optionally can be contained can be substituted by 1–2 carboxy, 1–2 sulfo or 1–2 hydroxy groups, T stands for a —CO—α, —NHCO—α or —NHCS—α group, and α stands for the bonding site to the terminal nitrogen atoms of the last generation, of reproduction unit W.

Preferred are complexing agent radicals of general formula IA.

As preferred complexing agent radicals K, those can be mentioned in which in above-indicated formula IA, the C$_1$–C$_{20}$, and preferably C$_1$–C$_{12}$ alkylene chain that stands for U$^7$ contains the groups —CH$_2$, —CH$_2$NHCO, —NHCOCH$_2$O, —NHCOCH$_2$OC$_6$H$_4$, —N(CH$_2$CO$_2$H),
—NHCOCH$_2$C$_6$H$_4$, —NHCSNHC$_6$H$_4$, —CH$_2$OC$_6$H$_4$, —CH$_2$CH$_2$O and/or is substituted by groups —COOH, —CH$_2$COOH.

As examples for U$^7$, the following groups can be cited:
—CH$_2$—, —CH$_2$CH$_2$—, —CH$_2$CH$_2$CH$_2$—, —C$_6$H$_4$—, —C$_6$H$_{10}$—, —CH$_2$C$_6$H$_5$—,
—CH$_2$NHCOCH$_2$CH(CH$_2$CO$_2$H)—C$_6$H$_4$—,
—CH$_2$NHCOCH$_2$OCH$_2$—,
—CH$_2$NHCOCH$_2$C$_6$H$_4$—,

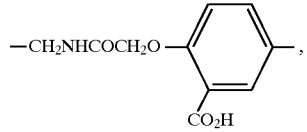

—CH$_2$NHCSNH—C$_6$H$_4$—CH(CH$_2$COOH)CH$_2$—,
—CH$_2$OC$_6$H$_4$—N(CH$_2$COOH)CH$_2$—,
—CH$_2$NHCOCH$_2$O(CH$_2$CH$_2$O)$_4$—C$_6$H$_4$—,
—CH$_2$O—C$_6$H$_4$—,
—CH$_2$CH$_2$—O—CH$_2$CH$_2$—, —CH$_2$CH$_2$—O—CH$_2$CH$_2$—O—CH$_2$CH$_2$—,

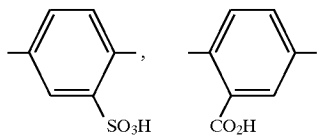

Especially preferably, U$^7$ stands for the CH$_2$—group.
As examples for R$^4$, the following groups can be indicated:

—CH$_3$, —C$_6$H$_5$, —CH$_2$—COOH,
—CH$_2$—C$_6$H$_5$, —CH$_2$—O—(CH$_2$CH$_2$—O—)$_6$CH$_3$,
—CH$_2$—OH

Preferred are the hydrogen atom and the methyl group.
T preferably stands for the —CO—d group.

If the agent according to the invention is intended for use in NMR diagnosis, the central ion of the complex salt must be paramagnetic. These are especially the divalent and trivalent ions of the elements of atomic numbers 21–29, 42, 44, and 58–70. Suitable ions are, for example, the chromium (III), iron(II), cobalt(II), nickel(II), copper(II), praseodymium(III), neodymium(III), samarium(III), and ytterbium(III) ions. Because of their very strong magnetic moment, the gadolinium(III), terbium(III), dysprosium(III), holmium(III), erbium(III), manganese(II), and iron(III) ions are especially preferred.

If the agent according to the invention is intended for use in diagnostic radiology, the central ion has to be derived from an element of higher atomic number in order to achieve sufficient absorption of the x rays. It has been found that for this purpose, diagnostic agents which contain a physiologically compatible complex salt with central ions of elements of atomic numbers between 21–29, 39, 42, 44, 57–83 are suitable; these are, for example, the lanthanum(III) ion and the above-mentioned ions of the lanthanide series.

The cascade polymer complexes according to the invention contain at least 16 ions of an element of the above-mentioned atomic numbers.

The remaining acid hydrogen atoms, i.e., those which were not substituted by the central ion, optionally can be replaced completely or partially by cations of inorganic and/or organic bases, amino acids, or amino acid amides.

Suitable inorganic cations are, for example, the lithium ion, the potassium ion, the calcium ion, the magnesium ion, and especially the sodium ion. Suitable cations of organic bases are, i.a., those of primary, secondary, or tertiary amines, such as, for example, ethanolamine, diethanolamine, morpholine, glucamine, N,N-dimethylglucamine, and especially N-methylglucamine. Suitable cations of amino acids are, for example, those of lysine, arginine, and ornithine, as well as the amides of otherwise acidic or neutral amino acids.

The compounds according to the invention, which have a molecular weight of 10,000–80,000 D, preferably 15,000–40,000 D, exhibit the desired properties described above. They contain the large number, required for their use, of metal ions bound in a stable manner in the complex.

They accumulate in regions with high vascular permeability, such as, e.g., in tumors, they make it possible to make statements regarding the perfusion of tissues, and they provide the possibility of determining the blood volume in tissues, of shortening selectively the relaxation times or densities of the blood, and of graphically representing the permeability of blood vessels. Such physiological data cannot be obtained through the use of extracellular contrast media, such as, e.g., Gd-DTPA [Magnevist$^{(R)}$]. From these standpoints, there also follow the uses in the modern imaging processes of nuclear spin tomography and computer tomography: more specific diagnoses of malignant tumors, early therapy monitoring in cases where cytostatic, antiphlogistic, or vasodilative therapy is used, early identification of underperfused regions (e.g., in the myocardium), angiography in vascular diseases, and identification and diagnosis of (sterile or infectious) inflammations.

As further advantages relative to extracellular contrast media, such as, e.g., Gd-DTPA [Magnevist$^{(R)}$], the greater effectiveness [of the compounds of the invention] as contrast media for nuclear spin tomography (higher relaxivity) must be emphasized; this ensures a marked reduction of the diagnostically required dose. At the same time, the contrast media according to the invention can be formulated as solutions in an isomolar manner in the blood and thus reduce the osmotic stress of the body, which is reflected in a reduced toxicity on the part of the substance (higher toxic threshold). Smaller doses and higher toxic thresholds result in a significant increase of the reliability of contrast medium use in modern imaging processes.

In comparison with macromolecular contrast media based on carbohydrates, e.g., dextran (European Patent Application, Publication No. 0 326 226), which carry — as mentioned — generally only about 5% of the signal-enhancing paramagnetic cation, the polymer complexes according to the invention exhibit a content of the paramagnetic cation of generally about 20%. Thus, the macromolecules according to the invention produce much better signal enhancement per molecule, which simultaneously has the effect that the dose necessary for nuclear spin tomography is considerably smaller relative to macromolecular contrast media based on carbohydrates.

With the polymer complexes according to the invention, it has been possible to design and produce macromolecules in such a way that the latter have a uniformly defined molecular weight. It is thus possible, surprisingly enough, to control the size of the macromolecules in such a way that the latter are large enough to be able to leave the vascular space only slowly, but at the same time small enough to be able to pass through the capillaries of the kidneys, which are 300–800 Å in size.

In comparison to the other mentioned polymer compounds of the prior art, the cascade polymer complexes according to the invention are distinguished by improved excretion behavior, greater effectiveness, greater stability, and/or better compatibility.

Another advantage of this invention lies in the fact that now complexes with hydrophilic or lipophilic, macrocyclic or open-chain, low-molecular, or high-molecular ligands have become accessible. As a result, the possibility exists for controlling the compatibility and pharmacokinetics of these polymer complexes by chemical substitution.

The production of the cascade polymer complexes according to the invention takes place in that compounds of general formula I'

$$A-\{X-[Y-(Z-(W-\beta_w)_z)_y]_x\}_a \qquad (I'),$$

in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, a stands for numbers 2 to 12, x, y, z and w, independently of one another, stand for numbers 1 to 4 and β stands for the bonding site of the terminal NH groups of the last generation, of reproduction unit W provided that at least two reproduction units are different, that for the product of multiplicities, $$16 < a \cdot x \cdot y \cdot z \cdot w < 64,$$

holds true, and that at least one of cascade reproduction units X, Y, Z, W stands for a 1,4,7,10-tetraazacyclododecane or 1,4,8,11-tetraazacyclotetradecane reproduction unit, with a complex or complexing agent K' of general formula I'A, I'B or I'C

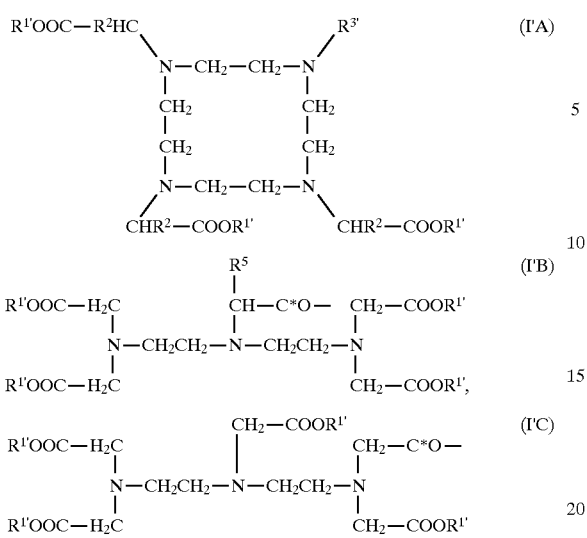 (I'A)

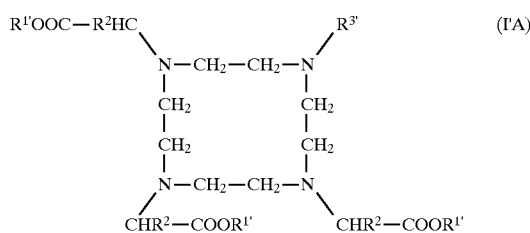 (I'B)

(I'C)

in which
- $R^{1'}$, independently of one another, stand for a hydrogen atom, a metal ion equivalent of atomic numbers 20–29, 39, 42–44, or 57–83 or an acid protective group,
- $R^2$ stands for a hydrogen atom, a methyl or an ethyl radical which optionally is substituted with 1–2 hydroxy or 1 carboxy group(s),
- $R^{3'}$ stands for a

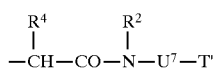

group or a

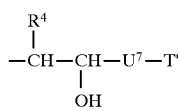

group
- $R^4$ stands for a hydrogen atom or a straight-chain, branched, saturated or unsaturated $C_1$–$C_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s),
- $R^5$ stands for a hydrogen atom or for $R^4$,
- $U^7$ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), and the phenylene groups that are optionally contained can be substituted by 1–2 carboxy, 1–2 sulfa or 1–2 hydroxy groups,
- T' stands for a —C*O, —COOH, —N=C=O or —N=C=S group, and C*O stands for an activated carboxyl group, provided that —if K' stands for a complex— at least two (in the case of divalent metals) or three (in the case of trivalent metals) of substituents $R^1$ stand for a metal ion equivalent of the above-mentioned elements and that optionally other carboxyl groups are present in the form of their salts with inorganic and/or organic bases, amino acids or amino acid amides, are reacted, optionally present protective groups are cleaved, the thus obtained cascade polymers —if K' stands for a complexing agent— are reacted in a way known in the art with at least one metal oxide or metal salt of an element of atomic numbers 20–29, 39, 42, 44, or 57–83 and then optionally in the cascade polymer complexes thus obtained, acid hydrogen atoms that are still present are completely or partially substituted by cations of inorganic and/or organic bases, amino acids, or amino acid amides, and optionally still present free terminal amino groups are optionally acylated —before or after the metal complexing.

Another aspect of this invention is represented by the new compounds of general formula I'A

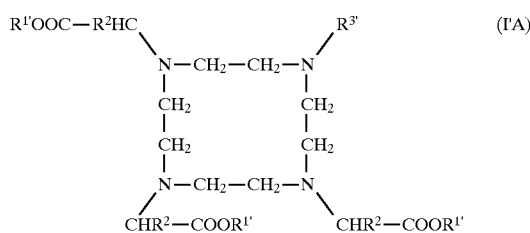 (I'A)

in which
- $R^{1'}$, independently of one another, stand for a hydrogen atom, a metal ion equivalent of atomic numbers 20–29, 39, 42–44 or 57–83 or an acid protective group,
- $R^2$ stands for a hydrogen atom, a methyl or an ethyl radical, which optionally is substituted with 1–2 hydroxy or 1 carboxy group(s),
- $R^{3'}$ stands for a

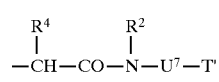

group or a

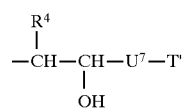

group
- $R^4$ stands for a hydrogen atom or a straight-chain, branched, saturated or unsaturated $C_1$–$C_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s),
- $U^7$ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), and the phenylene groups that are optionally contained can be substituted by 1–2 carboxy, 1–2 sulfo or 1–2 hydroxy groups, T' stands for a —C*O, —COOH, —N=C=O or —N=C=S group, and C*O stands for an activated carboxyl group.

They are used as important intermediate products for the production of the cascade polymer complexes of general formula I.

As an example of an activated carbonyl group C*O in complexes or complexing agents K', anhydride, p-nitrophenyl ester, N-hydroxysuccinimide ester, pentafluorophenyl ester, and acid chloride can be mentioned.

The addition or acylation that is carried out to introduce the complexing agent units is performed with substrates that contain desired substituents K (optionally bound to a leaving group) or from which the desired substituent is generated by the reaction.

As examples of addition reactions, the reaction of isocyanates and isothiocyanates can be mentioned, in which the reaction of isocyanates is preferably performed in aprotic solvents, such as, e.g., THF, dioxane, DMF, DMSO, methylene chloride at temperatures of between 0° and 100° C., preferably between 0° and 50° C., optionally with the addition of an organic base such as triethylamine, pyridine, lutidine, N-ethyldiisopropylamine, N-methylmorpholine. The reaction with isothiocyanates is generally performed in solvents, such as, e.g., water or lower alcohols, such as, e.g., methanol, ethanol, isopropanol or their mixtures, DMF or mixtures of DMF and water at temperatures of between 0° and 100° C., preferably between 0° and 50° C., optionally with the addition of an organic or inorganic base, such as, e.g., triethylamine, pyridine, lutidine, N-ethyldiisopropylamine, N-methylmorpholine, or alkaline-earth hydroxides, alkali hydroxides, such as, e.g., lithium, sodium, potassium, calcium hydroxide, or their carbonates, such as, e.g., magnesium carbonate.

As examples of acylation reactions, the reaction of free carboxylic acids according to the methods known to one skilled in the art [e.g., J. P. Greenstein, M. Winitz, Chemistry of the Amino Acids, John Wiley & Sons, N.Y. (1961), pp. 943–945) can be mentioned. It has proven advantageous, however, to convert the carboxylic acid group before the acylation reaction to an activated form, such as, e.g., anhydride, active ester or acid chloride [e.g., E. Gross, J. Meienhofer, The Peptides, Academic Press, N.Y. (1979), Vol. 1, pp. 65–314; N. F. Albertson, Org. React. 12, 157 (1962)].

In the case of reaction with active ester, the literature known to one skilled in the art [e.g., Houben-Weyl, Methoden der organischen Chemie [Methods of Organic Chemistry], Georg Thieme Verlag, Stuttgart, Volume E 5 (1985), 633] can be cited. This reaction can be performed under the conditions indicated above for the anhydride reaction. However, aprotic solvents, such as, e.g., methylene chloride, chloroform, can also be used.

In the case of acid chloride reactions, only aprotic solvents, such as, e.g., methylene chloride, chloroform, toluene or THF, at temperatures between -20° to 50° C., preferably between 0° to 30° C., are used. Further, literature known to one skilled in the art [e.g., Houben-Weyl, Methoden der Organischen Chemie, Georg-Thieme-Verlag, Stuttgart, (1974), Volume 15/2, pp. 355–364] can be cited.

If $R^{1'}$ stands for an acid protective group, lower alkyl, aryl and aralkyl groups, for example, the methyl, ethyl, propyl, butyl, phenyl, benzyl, diphenylmethyl, triphenylmethyl, bis-(p-nitrophenyl)-methyl groups, as well as trialkylsilyl groups, are suitable.

The optionally desired cleavage of the protective groups takes place according to the processes known to one skilled in the art, for example by hydrolysis, hydrogenolysis, alkaline saponification of esters with alkali in aqueous-alcoholic solution at temperatures of 0° C. to 50° C. or in the case of tert-butyl esters with the aid of trifluoroacetic acid.

Terminal amino groups that are optionally incompletely acylated with ligands or complexes can optionally be converted to amides or semiamides. The reactions with acetic anhydride, succinic anhydride or diglycolic anhydride can be mentioned as examples.

The introduction of the desired metal ions takes place in the way in which it was disclosed, e.g., in German laid-open specification 34 01 052, by the metal oxide or a metal salt (for example, the nitrate, acetate, carbonate, chloride or sulfate) of the element of atomic numbers 20–29, 42, 44, 57–83 being dissolved or suspended in water and/or a lower alcohol (such as methanol, ethanol or isopropanol) and being reacted with the solution or suspension of the equivalent amount of complexing ligand and then optionally existing acid hydrogen atoms of the acid groups being substituted by cations of inorganic and/or organic bases, amino acids or amino acid amides.

The introduction of the desired metal ions can take place both in the stage of complexing agent I'A or I'B, i.e., before the coupling to the cascade polymers, and after coupling of unmetalated ligands I'A, I'B or I'C.

In this case, the neutralization takes place with the aid of inorganic bases (for example, hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methyl and N,N-dimethylglucamine, as well as basic amino acids, such as, for example, lysine, arginine and ornithine or of amides of originally neutral or acid amino acids, such as, for example, hippuric acid, glycine acetamide.

For the production of neutral complex compounds, enough of the desired bases can be added, for example, to the acid complex salts in aqueous solution or suspension that the neutral point is reached. The obtained solution can then be evaporated to dryness in a vacuum. Often, it is advantageous to precipitate the formed neutral salts by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others) and thus to obtain easily isolated and readily purified crystallizates. It has proven especially advantageous to add the desired bases as early as during the complexing of the reaction mixture and thus to save a process step.

If the acid complex compounds contain several free acid groups, it is often suitable to produce neutral mixed salts, which contain both inorganic and organic cations as counterions.

This can happen, for example, by the complexing ligands in aqueous suspension or solution being reacted with the oxide or salt of the element yielding the central ion and half of the amount of an organic base required for neutralization, the formed complex salt being isolated, optionally purified and then mixed with the required amount of inorganic base for complete neutralization. The sequence of the addition of base can also be reversed.

The purification of the thus obtained cascade polymer complexes takes place, optionally after adjusting the pH to 6 to 8, preferably about 7, by adding an acid or base, preferably by ultrafiltration with membranes of suitable pore size (e.g., Amicon$^{(R)}$XM30, Amicon$^{(R)}$YM10, Amicon$^{(R)}$YM3) or gel filtration on, e.g., suitable Sephadex$^{(R)}$ gels.

In the case of neutral complex compounds, it is often advantageous to provide the polymeric complexes with an anion exchanger, for example, IRA 67 (OH⁻ form) and optionally in addition with a cation exchanger, for example, IRC 50 (H⁺ form) for the separation of ionic components.

The production of the cascade polymers carrying terminal amino groups required for the coupling to complexing agents K' (or else the corresponding metal-containing complexes) generally proceeds from nitrogen-containing cascade starters $A(H)_a$ that can be produced by commercially available methods or according to or analogously to methods known in the literature. The introduction of generations X, Y, Z and W takes place according to methods known in the literature [e.g., J. March, Advanced Organic Chemistry, 3rd ed.; John Wiley & Sons, (1985), 364–381] by acylation or alkylation reactions with protected amines exhibiting the desired structures, which contain functional groups capable of bonding to the cascade nuclei, such as, e.g., carboxylic acids, isocyanates, isothiocyanates or activated carboxylic acids (such as, e.g., anhydrides, active esters, acid chlorides) or halides (such as, e.g., chlorides, bromides, iodides), aziridine, mesylates, tosylates or other leaving groups known to one skilled in the art.

It can be stressed, however, that the differentiation between cascade nucleus A and reproduction units is purely formal. It can be advantageous synthetically that formal cascade starter $A(H)_a$ is not used, but rather the nitrogen atoms forming part of the cascade nucleus by definition are introduced first together with the first generation. Thus, e.g., for synthesis of the compound described in Example 1b), it is more advantageous not to alkylate the formal cascade nucleus trimesic acid triamide with e.g., benzyloxycarbonylaziridine (six-fold), but to react trimesic acid trichloride with bis[2-(benzyloxycarbonylamino)-ethyl]-amine (three-fold).

In the same way, with the incorporation of the necessarily present 1,4,7,10-tetraazacyclododecane ("cyclene") or 1,4,8,11-tetraazacyclotetradecane ("cyclam") reproduction units, it can be advantageous not to synthesize the cascade polymer formally shell for shell.

Thus, it is possible, for example, in an upstream reaction step, to bind the reproduction unit following a cyclene shell to three nitrogen atoms of the cyclene. Then, after functionalization of the fourth cyclene-nitrogen, both reproduction units can be linked simultaneously to the increasing cascade.

As amino protective groups, the benzyloxycarbonyl, tert-butoxycarbonyl, trifluoroacetyl, fluorenylmethoxycarbonyl, benzyl and formyl groups familiar to one skilled in the art [Th. W. Greene, P. G. M. Wuts, Protective Groups in Organic Syntheses, 2nd ed, John Wiley and Sons (1991), pp. 309–385] can be mentioned. After cleavage of these protective groups, which also can take place according to methods known in the literature, the next desired generation can be introduced into the molecule. In addition to this synthesis of a generation consisting of two reaction stages in each case (alkylation or acylation and protective group cleavage), the simultaneous introduction of two, e.g., $X—[Y]_x$, or several generations, e.g., $X—[Y—(Z)_Y]_x$, is also possible with only two reaction stages. The synthesis of these multi-generation units takes place by alkylation or acylation of unprotected amines ("reproduction amine"), exhibiting the structures of the desired reproduction units, with a second reproduction amine, whose amine groups are present in protected form.

The compounds of general formula $A(H)_a$ required as cascade starters are commercially available or can be produced according to or analogously to methods known in the literature [e.g., Houben-Weyl, Methoden der Org. Chemie, Georg-Thieme-Verlag, Stuttgart (1957), Vol. 11/1; M. Micheloni et al., Inorg. Chem. (1985), 24, 3702; T. J. Atkins et al., Org. Synth., Vol. 58 (1978), 86–98; The Chemistry of Heterocyclic Compounds: J. S. Bradshaw et al., Aza-Crown-Macrocycles, John Wiley & Sons, N.Y. (1993)]. As examples, there can be cited:

Tris(aminoethyl)amine [e.g., Fluka Chemie [Fluka Chemistry] AG, Switzerland; Aldrich-Chemie [Aldrich Chemistry], Germany];

tris(aminopropyl)amine [e.g., C. Woerner et al., Angew. Chem. [Applied Chem.] Int. Ed. Engl. (1993), 32, 1306];

diethylenetriamine [e.g., Fluka; Aldrich];

triethylenetetramine [e.g., Fluka; Aldrich];

tetraethylenepentamine [e.g., Fluka; Aldrich];

1,3,5-tris(aminomethyl)benzene [e.g., T. M. Garrett et al., J. Am. Chem. Soc. (1991), 113, 2965];

trimesic acid triamide [e.g., H. Kurihara; Jpn. Kokai Tokyo Koho JP 04077481; CA 117, 162453];

1,4,7-triazacyclononane [e.g., Fluka; Aldrich];

1,4,7,10,13-pentaazacyclopentadecane [e.g., K. W. Aston, Eur. Pat. Appl. 0 524 161, CA 120, 44580];

1,4,7,10-tetraazacyclododecane [e.g., Aldrich] 1,4,8,11-tetraazacyclotetradecane [e.g., Fluka; Aldrich];

1,4,7,10,13,16,19,22,25,28-Decaazacyclotriacontane [e.g., A. Andres et al., J. Chem. Soc. Dalton Trans. (1993), 3507];

1,1,1-tris(aminomethyl)ethane [e.g., R. J. Geue et al., Aust. J. Chem. (1983), 36, 927];

tris(aminopropyl)-nitromethane [e.g., G. R. Newkome et al., Angew. Chem. 103, 1205 (1991) analogously to R. C. Larock, Comprehensive Organic Transformations, VCH Publishers, N.Y. (1989), 419–420]

1,3,5,7-adamantanetetracarboxylic acid amide [e.g., H. Stetter et al., Tetr. Lett. 1967, 1841];

1,2-bis[phenoxyethane]-3', 3", 5', 55"-tetracarboxylic acid amide [e.g., J. P. Collman et al.; J. Am. Chem. Soc. (1988), 110, 3477–86 analogously to the instructions for Example 1b)];

1,4,7,10,13,16,21,24-octaazabicyclo[8.8.8.]hexacosane [e.g., P. H. Smith et al., J. Org. Chem. (1993), 58, 7939].

The production of the reproduction amines that contain the above-mentioned functional groups required for the synthesis of generations takes place according to or analogously to the instructions described in the experimental part or according to processes known in the literature.

As examples, there can be mentioned $N^\alpha,N^{86}$-Di-benzyloxycarbonyl-lysine-p-nitrophenyl ester;

$HOOC-CH_2OCH_2CO-N(CH_2CH_2NH-CO-O-CH_2C_6H_5)_2$;

$HOOC-CH_2N(CH_2CH\ NH-CO-O-CH_2C_6H_5)_2$;

$HOOC-CH_2CH_2CO-N(CH_2CH_2NH-COCF_3)_2$ [to be produced according to instructions for Example 5a), by starting from bis(trifluoroacetylaminoethyl)amine instead of bis(benzyloxycarbonylaminoethyl)amine;

$HOOC-CH_2OCH_2CONH-C_6H_4-CH[CH_2CON(CH_2CH_2NH-CO-O-CH_2C_6H_5)_2]_2$;

$O=C=N-C_6H_4-CH[CH_2CON(CH_2CH_2NH-CO-O-CH_2C_6H_5)_2]_2$

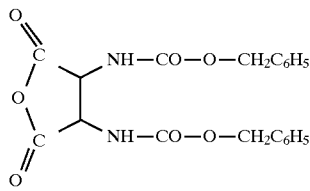

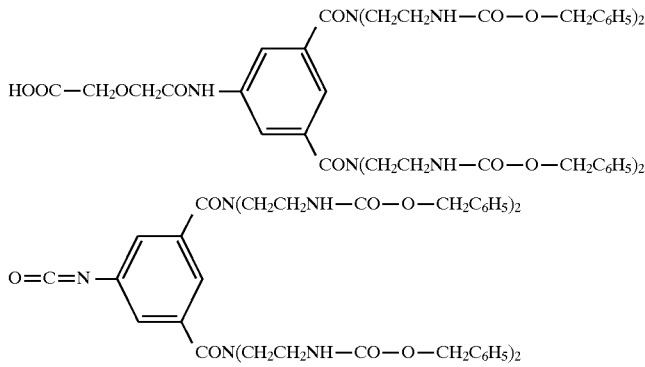

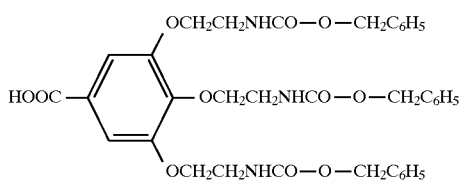

N-benzyloxycarbonyl-aziridine to be produced according to M. Zinic et al., J. Chem. Soc, Perkin Trans 1, 21–26 (1993)

N-benzyloxycarbonyl-glycine commercially available in, e.g., Bachem, Calif.

to be produced according to C. J. Cavallito et al., J. Amer. Chem. Soc. 1943, 65, 2140, by starting from N—CO—O—H$_2$C$_6$H$_5$-(2-bromoethyl)amine instead of benzyl chloride [A. R. Jacobson et al., J. Med. Chem. (1991), 34, 2816].

The production of the complexes and complexing agents of general formula I'A and I'B takes place according to or analogously to the instructions described in the experimental part or according to methods known in the literature (see, e.g., European Patent Applications Nos. 0 512 661, 0 430 863, 0 255 471 and 0 565 930.

Thus, the production of compounds of general formula I'A is carried out, e.g., in that a group T''' is used as a precursor of functional group T', either in the meaning of a protected acid function, which can be converted to the free acid function independently of acid protective groups R$^{1'}$ according to the above-indicated process, or in the meaning of a protected amine function, which unblocks according to processes known in the literature [Th. W. Greene, P. G. M. Wuts, Protective Groups in Organic Synthesis, 2nd edition, John Wiley & Sons (1991), pp. 309–385] and then can be converted to the isocyanates or isothiocyanates [Methoden der Org. Chemie (Houben-Weyl), E 4, pp. 742–749, 837–843, Georg Thieme Verlag, Stuttgart, N. Y. (1983)]. Such compounds can be produced according to or analogously to the instructions that are described in the experimental part by monoalkylation of cyclene with suitable α-halogenated acid amides [in aprotic solvents, such as, e.g., chloroform].

The production of compounds of general formula I'B can be carried out, for example, in that a protected acid function is used as a precursor of the activated carboxyl group-C*O, which can be converted to the free acid function independently of acid protective groups R$^{1'}$ according to the above-indicated processes and can be activated according to the processes that are known in the literature and are also described above. Such compounds can be produced according to or analogously to the instructions that are described in the experimental part or, for example, in that an amino acid derivative of general formula II

in which

R$^{5'}$ has the meaning indicated for R$^5$, and hydroxy or carboxy groups that are optionally contained in R$^5$ are optionally present in protected form, and V$^1$ is a straight-chain or branched C1–C6 alkyl group, a benzyl, trimethylsilyl, triisopropylsilyl, 2,2,2-trifluoroethoxy or 2,2,2-trichloroethoxy group, in which V$^1$ is different from R$^{1''}$, is reacted with an alkylating agent of general formula III

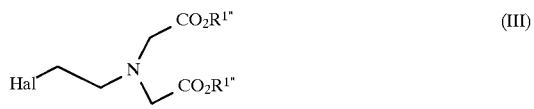

in which

R$^{1''}$ stands for a protective group, and

Hal stands for a halogen atom, such as Cl, Br or I, but preferably Cl [see also M. A. Williams, H. Rapoport, J. Org. Chem. 58, 1151 (1993)].

Preferred amino acid derivatives are the esters of naturally occurring α-amino acids.

The reaction of compound (II) with compound (III) is carried out preferably in a buffered alkylation reaction, in which an aqueous phosphate-buffer solution is used as buffer. The reaction is carried out at a pH of 7–9, but preferably at a pH of 8. The buffer concentration can be between 0.1–2.5M, but preferably a 2M phosphate-buffer solution is used. The temperature of the alkylation can be between 0° and 50° C.; the preferred temperature is room temperature.

The reaction is carried out in a polar solvent, such as, e.g., acetonitrile, tetrahydrofuran, 1,4-dioxane or 1,2-dimethoxyethane. Preferably, acetonitrile is used.

The production of the pharmaceutical agents according to the invention takes place also in a way known in the art, by the complex compounds according to the invention—optionally with the addition of the additives usual in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriaminepentaacetic acid or the corresponding Ca-cascade polymer complexes) or—if necessary—electrolytes, such as, for example, sodium chloride or—if necessary—antioxidants, such as, for example, ascorbic acid.

If suspensions or solutions of the agents according to the invention in water or physiological salt solution are desired for enteral administration or other purposes, they are mixed with one or more adjuvant(s) usual in galenicals [for example, methylcellulose, lactose, mannitol] and/or surfactant(s) [for example, lecithins, Tween(R), Myrj(R)] and/or flavoring substance(s) for taste correction [for example, ethereal oils].

In principle, it is also possible to produce the pharmaceutical agents according to the invention even without isolating the complex salts. In any case, special care must be used to undertake the chelation so that the salts and salt solutions according to the invention are practically free of noncomplexed metal ions having a toxic effect.

This can be assured, for example, with the aid of color indicators such as xylenol orange by control titrations during the production process. The invention therefore also relates to processes for the production of complex compounds and their salts. As a last precaution, there is a purification of the isolated complex salt.

The pharmaceutical agents according to the invention contain preferably 1 µmol-1 mol/l of the complex salt and are generally dosed in amounts of 0.0001–5 mmol/kg. They are intended for enteral and parenteral administration. The complex compounds according to the invention are used 1. for NMR diagnosis and diagnostic radiology in the form of their complexes with the ions of elements with atomic numbers 21–29, 39, 42, 44 and 57–83;
2. for radiodiagnosis and radiotherapy in the form of their complexes with radioisotopes of the elements with atomic numbers 27, 29, 31, 32, 37–39, 43, 49, 62, 64, 70, 75 and 77.

The agents according to the invention meet the varied requirements for suitability as contrast media for nuclear spin tomography. Thus, they are very well suited, after oral or parenteral administration, for improving the image, obtained with the aid of nuclear spin tomographs, in its informative value by increasing the signal intensity. Further, they show the great effectiveness which is necessary to load the body with the fewest possible amounts of foreign substances, and the good compatibility which is necessary to maintain the noninvasive nature of the studies.

The good water solubility and low osmolality of the agents according to the invention makes it possible to produce highly concentrated solutions, so that the volume load of the circulatory system can be held within reasonable limits, and to compare the dilution through the bodily fluid, i.e., NMR diagnostic agents must be 100- to 1000-fold better water-soluble than for NMR spectroscopy. Further, the agents according to the invention exhibit not only a high stability in vitro, but also a surprisingly high stability in vivo, so that a release or an exchange of the ions—toxic in themselves—not covalently bound in the complexes, in which the new contrast media are again completely excreted, takes place only extremely slowly.

In general, the agents according to the invention for use as NMR diagnostic agents are dosed in amounts of 0.0001–5 mmol/kg, preferably 0.005–0.5 mmol/kg. Details of use are discussed, for example, in H. -J. Weinmann et al., Am. J. of Roentgenology 142, 619 (1984).

Especially low dosages (under 1 mg/kg of body weight) of organ-specific NMR diagnostic agents can be used, for example, to detect tumors and myocardial infarction.

Further, the complex compounds according to the invention are used advantageously as susceptibility reagents and as shift reagents for in vivo NMR spectroscopy.

The agents according to the invention are also suitable as radiodiagnostic agents because of their advantageous radioactive properties and the good stability of the complex compounds contained in them. Details of their use and dosage are described, e.g., in "Radiotracers for Medical Applications," CRC Press, Boca Raton, Fla.

Another imaging method with radioisotopes is positron emission tomography, which uses positron-emitting isotopes, such as, e.g., $^{43}$Sc, $^{44}$Sc, $^{52}$Fe, $^{55}$Co and $^{68}$Ga (Heiss, W. D.; Phelps, M. E.; Positron Emission Tomography of the Brain, Springer Verlag Berlin, Heidelberg, N. Y. 1983).

The compounds according to the invention are surprisingly also suitable for differentiating malignant and benign tumors in areas without blood-brain barriers.

They are also distinguished in that they are eliminated completely from the body and thus are well compatible.

Since the substances according to the invention are concentrated in malignant tumors (no diffusion in healthy tissue, but high permeability of tumor vessels), they can also assist in the radiation therapy of malignant tumors. The latter is distinguished from the corresponding diagnosis only by the amount and type of the isotope used. The object, in this case, is the destruction of tumor cells by high-energy shortwave radiation with a smallest possible range of action. For this purpose, interactions of the metals contained in the complexes (such as, e.g., iron or gadolinium) are used with ionizing radiations (e.g., x rays) or with neutron rays. By this effect, the local radiation dose is significantly increased on the spot where the metal complex is found (e.g., in tumors). To produce the same radiation dose in the malignant tissue, the radiation exposure for healthy tissue can be considerably reduced with the use of such metal complexes and thus side effects that are stressful to the patients are avoided. The metal complex conjugates according to the invention are therefore suitable also as radiosensitizing substances in radiation therapy of malignant tumors (e.g., use of Mössbauer effects or in neutron capture therapy). Suitable β-emitting ions are, for example, $^{46}$Sc, $^{47}$Sc, $^{48}$Sc, $^{72}$Ga, $^{73}$Ga and 90Y. Suitable α-emitting ions exhibiting small half-lives are, for example, $^{211}$Bi, $^{212}$Bi, $^{213}$Bi and $^{214}$Bi, and $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy proposed by R. L. Mills et al. (Nature Vol. 336, (1988), p. 787), the central ion must be derived from a Mössbauer isotope, such as, for example, $^{57}$Fe or $^{151}$Eu.

In the in vivo administration of the therapeutic agents according to the invention, the latter can be administered together with a suitable vehicle, such as, for example, serum, or physiological common salt solution and together with another protein, such as, for example, human serum albumin. In this case, the dosage depends on the type of cellular disorder, the metal ion used and the type of imaging method.

The therapeutic agents according to the invention are administered parenterally, preferably i.v.

Details of use of radiotherapeutic agents are discussed, e.g., in R. W. Kozak et al. TIBTEC, Oct. 1986, 262.

The agents according to the invention are very well suited as x-ray contrast media, and it is especially to be emphasized that no signs of the anaphylaxis-like reactions, known from the iodine-containing contrast media, can be detected in biochemical-pharmacological studies. They are especially valuable because of the advantageous absorption properties in the areas of higher tube voltages for digital subtraction techniques.

In general, the agents according to the invention are dosed for use as x-ray contrast media analogously to, for example, meglumine-diatrizoate in amounts of 0.1–5 mmol/kg, preferably 0.25–1 mmol/kg.

Details of use of x-ray contrast media are discussed, for example, in Barke, Röntgenkontrastmittel [X-Ray Contrast Media], G. Thieme, Leipzig (1970) and P. Thurn, E. B ücheler "Einführung in die Röntgendiagnostik [Introduction to Diagnostic Radiology]," G. Thieme, Stuttgart, N. Y. (1977).

In general, it has been possible to synthesize new complexing agents, metal complexes and metal complex salts, which open up new possibilities in diagnostic and therapeutic medicine.

Figure 1:
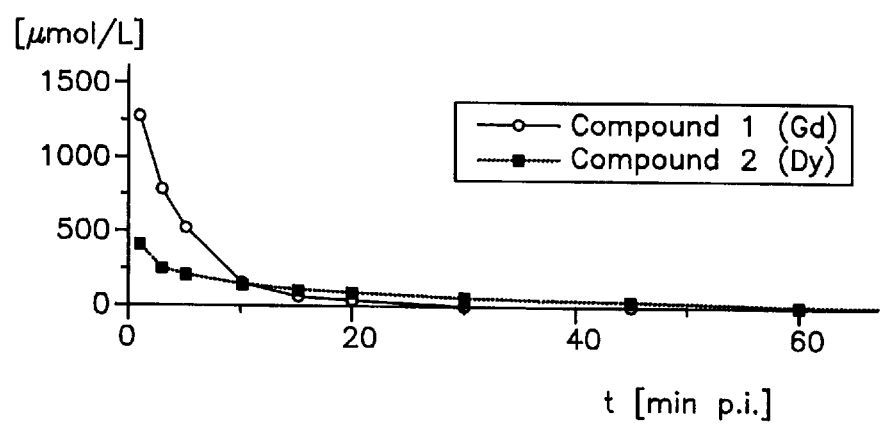
FIG. 1 shows measured blood concentrations of Gd (compound 1) and Dy (compound 2) in rats (n 3)

The following examples are used for a more detailed explanation of the object of the invention:

EXAMPLE 1 a) 1,4,7-Tris(N,N'-dibenzyloxycarbonyl-lysyl)-1,4,7, 10-tetraazacyclododecane 49.07 g (95.9 mmol) of di-Z-lysine-N-hydroxysuccinimide ester and 5 g (29 mmol) of cyclene (=1,4,7,10-tetraazacyclododecane) are dissolved in a mixture of 200 ml of toluene/100 ml of dioxane. 9.7 g (95.9 mmol) of triethylamine is added and heated for 12 hours to 70° C. It is evaporated to dryness, the residue is taken up in 600 ml of dichloromethane and extracted 3 times with 200 ml of 5% aqueous potassium carbonate solution each. The organic phase is dried on magnesium sulfate and evaporated to dryness in a vacuum. The residue is chromatographed on silica gel (mobile solvent: ethyl acetate/ethanol=15:1).

Yield: 29.61 g (75% of theory) of a colorless solid
Cld: C 65.28 H 6.81 N 10.29
Fnd: C 65.41 H 6.97 N 10.10 b) 1-(Carboxymethoxyacetyl)-4,7,10-tris(N,N'-dibenzyloxycarbonyl-lysyl)-1,4,7,10-tetraazacyclododecane 3.58 g (30.86 mmol) of diglycolic anhydride and 6.24 g (61.72 mmol) of triethylamine are added to 28 g (20.56 mmol) of the title compound of Example 1a (dissolved in 200 ml of tetrahydrofuran). It is heated for 6 hours to 50° C. The solution is evaporated to dryness in a vacuum, taken up with 300 ml of dichloromethane and extracted twice with 150 ml of 5% aqueous hydrochloric acid each. The organic phase is dried on magnesium sulfate, evaporated to dryness in a vacuum and the residue is chromatographed on silica gel (mobile solvent: dichloromethane/methanol=20:1).

Yield: 27.65 g (91% of theory) of a colorless solid
Elementary analysis
Cld: C 63.40 H 6.55 N 9.48
Fnd: C 63.21 H 6.70 N 9.27 c) 1-[5-(4-Nitrophenoxy)-3-oxaglutaryl]-4,7,10-tris(N,N'-dibenzyloxycarbonyl-lysyl)-1,4,7,10-tetraazacyclododecane 14.78 g (10 mmol) of the carboxylic acid described in Example 1b, dissolved in 150 ml of dichloromethane, is mixed first with 1.53 g (11 mmol) of 4-nitrophenol and then at 0° C. with 2.27 g (11 mmol) of dicyclohexylcarbodiimide. After stirring overnight at room temperature, it is suctioned off from dicyclohexylurea, the filtrate is concentrated by evaporation and reprecipitated from isopropanol. The mother liquor is decanted from the oily product that accumulates, the oil is taken up in dichloromethane and concentrated by evaporation in a vacuum. 15.4 g (96.3%) of foamy, solidified solid is obtained.

Elementary analysis
Cld: C 63.11 H 6.24 N 9.64
Fnd: C 62.98 H 6.31 N 9.80 d) Bis[2-(benzyloxycarbonylamino)-ethyl]-amine 51.5 g (500 mmol) of diethylenetriamine and 139 ml (1 mol) of triethylamine are dissolved in dichloromethane and mixed at -20° C. with 161 g of benzyl cyanoformate (Fluka) in dichloromethane and then stirred overnight at room temperature. After the reaction is completed, concentration by evaporation is performed during draw-off, the residue is taken up in diethyl ether, the organic phase is washed with sodium carbonate solution and dried with sodium sulfate. The filtrate is mixed with hexane, the precipitate is filtered out and dried.

Yield: 163.4 g (88% of theory)
Elementary analysis
Cld: C 64.67 H 6.78 N 11.31
Fnd: C 64.58 H 6.83 N 11.28 e) N,N,N',N',N",N"-Hexakis[2-(benzyloxycarbonylamino)-ethyl]-trimesic acid triamide 13.27 g (50 mmol) of trimesic acid trichloride (Aldrich) and 34.7 ml (250 mmol) of triethylamine are dissolved in dimethylformamide (DMF) and mixed at 0° C. with 65.0 g (175 mmol) of the amine described in Example 1d and then stirred overnight at room temperature. The solution is concentrated by evaporation in a vacuum, and the residue is chromatographed on silica gel with ethyl acetate.

Yield: 39.4 g (62% of theory)
Elementary analysis
Cld: C 65.24 H 5.95 N 9.92
Fnd: C 65.54 H 5.95 N 9.87 f) Completely protected benzyloxycarbonyl-36mer-polyamine, synthesized from N,N,N',N',N",N"-hexakis(2-aminoethyl)-trimesic acid triamide-core and six amine-protected hexaamine-monocarboxylic acids that are described in Example 1b 1.27 g (1 mmol) of the hexa-benzyloxycarbonylamine described in Example 1e is dissolved in glacial acetic acid and mixed with 33% hydrogen bromide in glacial acetic acid while being stirred. After 60 minutes, the incipient precipitation is completed with diethyl ether, the hexa-amine-hydrobromide produced is washed with ether, dried in a vacuum and further reacted without further purification.

Yield: 0.95 g (quantitative)

Then, the hexa-amine-hydrobromide is dissolved in 150 ml of DMF, mixed with 15.99 g (10 mmol) of the 4-nitrophenyl-activated ester described in Example 1c and with 4.05 g (40 mmol) of triethylamine, stirred overnight at room temperature and ultimately evaporated to dryness in a vacuum. The residue is taken up in ethyl acetate and washed in succession with water, diluted sodium hydroxide solution and saturated NaCl solution. The organic phase is dried on sodium sulfate, and the filtrate is evaporated to dryness, and the residue is chromatographed on silica gel (mobile solvent: dichloromethane/methanol 18:2).

Yield: 6.55 g (71% of theory) of a colorless solid
Elementary analysis
Cld: C 63.68 H 6.59 N 10.48
Fnd: C 63.83 H 6.70 N 10.29
MALDI-TOF mass spectrum: molar peak at 9246 (M+Na$^+$)

g) 1-(Benzyloxycarbonylmethyl)-4,7,10-tris(tert-butoxycarbonylmethyl)-1,4,7,10-tetraazacyclododecane (as sodium bromide complex)

20 g (38.87 mmol) of 1,4,7-tris(tert-butoxycarbonylmethyl)-1,4,7,10-tetraazacyclododecane (D03A-tris-tert-butyl ester, produced according to EP 0 299 795, Example 22a, is dissolved in 100 ml of acetonitrile. Then, 11.45 g (50 mmol) of bromoacetic acid benzyl ester and 10.6 g (100 mmol) of sodium carbonate are added and stirred for 12 hours at 60° C. The salts are filtered out, the filtrate is evaporated to dryness in a vacuum, and the residue is chromatographed on silica gel (mobile solvent: methylene chloride/methanol=20:1).

Yield: 21.72 g (73% of theory) of a colorless amorphous powder
Elementary analysis
Cld: C 54.90 H 7.63 N 7.32 Na 3.00 Br 10.44
Fnd: C 54.80 H 7.72 N 7.21 Na 2.89 Br 10.27 h) 1-(Carboxymethyl)-4,7,10-tris(tert-butoxycarbonylmethyl)-1,4,7,10-tetraazacyclododecane (as sodium bromide complex)

20 g (26.12 mmol) of the title compound of Example 1q is dissolved in 300 ml of isopropanol, and 3 g of palladium catalyst (10% Pd/C) is added. It is hydrogenated overnight at room temperature. The catalyst is filtered out, and the filtrate is evaporated to dryness.

Yield: 17.47 g (99% of theory) of a colorless amorphous powder
Elementary analysis
Cld: C 49.78 H 7.76 N 8.29 Na 4.44 Br 11.83
Fnd: C 49.59 H 7.59 N 8.17 Na 4.40 Br 11.70 i) 1-(4-Carboxy-2-oxo-3-azabutyl)-4,7,10-tris(tert-butoxycarbonylmethyl)-1,4,7,10-tetraazacyclododecane 1.73 g (15 mmol) of N-hydroxysuccinimide is added to 10 g (14.80 mmol) of the title compound of Example 1h in 100 ml of dimethylformamide and cooled to 0° C. Then, 4.13 g (20 mmol) of dicyclohexylcarbodiimide is added and stirred for 1 hour at 0° C. and then for 2 hours at room temperature. It is cooled off to 0° C. and then 5.1 g (50 mmol) of triethylamine and 2.25 g (30 mmol) of glycine are added. It is stirred overnight at room temperature. Precipitated urea is filtered out, and the filtrate is evaporated to dryness in a vacuum. The residue is taken up with water and extracted twice with methylene chloride. The organic phase is dried on magnesium sulfate and concentrated by evaporation in a vacuum. The residue is chromatographed on silica gel (mobile solvent: methylene chloride/methanol=15:1).

Yield: 8.20 g (88% of theory) of a colorless solid
Elementary analysis
Cld: C 57.21 H 8.80 N 11.12
Fnd: C 57.10 H 8.91 N 11.03 k) 36mer-N-(5-DO3A-yl-4-oxo-3-azapentanoyl)-cascade polyamide based on the 36mer-polyamine described in Example 1f [DO3A=1,4,7-tris(carboxymethyl)-1,4,7,10-tetraazacyclododecane] 1.84 (0.2 mmol) of the 36mer-benzyloxycarbonylamine described in Example 1f is dissolved in glacial acetic acid and mixed with 33% hydrogen bromide in glacial acetic acid while being stirred. After 5 hours, the incipient precipitation is completed with diethyl ether, the 36mer-amine-hydrobromide produced is washed with ether, dried in a vacuum and used without further purification in the reaction further described below.

Yield: 1.5 g (quantitative)

14.7 g (20 mmol) of the carboxylic acid described in Example 1i, 3.0 g (20 mmol) of 1-hydroxybenzotriazole and 6.4 g (20 mmol) of 2-(1H-benzotriazol-1-yl)-1,1,3,3-tetramethyl-uronium tetrafluoroborate (TBTU; Peboc Limited, UK) are dissolved in DMF and stirred for 15 minutes. The solution is then mixed with 10.3 ml (60 mmol) of N-ethyldiisopropylamine and with 1.5 g (0.2 mmol) of the above-described 36mer-amine-hydrobromide and stirred for 4 days at room temperature. After the reaction is completed, it is concentrated by evaporation in a vacuum, the residue is dissolved at 0° C. in trifluoroacetic acid, stirred overnight at room temperature, concentrated by evaporation in a vacuum and the residue is stirred up with ether. The substance is suctioned off, washed with ether, dried in a vacuum, ultimately dissolved in water, set at pH 7 with 2N sodium hydroxide solution, and the solution is purified with an Amicon$^{(R)}$-ultrafiltration membrane YM3 (cut off: 3000 Da). The retentate is then filtered and freeze-dried.

Yield: 3.61 g (72% of theory) of flocculent powder H$_2$O content (Karl-Fischer): 8.9%
Elementary analysis (relative to anhydrous substance)
Cld: C 44.86 H 5.87 N 15.34 Na 10.92
Fnd: C 45.09 H 5.80 N 15.44 Na 10.51 l) 36mer-Gd Complex of the ligand described in the example above 2.5 g (0.1 mmol) of the sodium salt of the complexing agent acid described in Example 1k) above is acidified in water with 5 ml of glacial acetic acid, mixed with 725 mg (2 mmol) of Gd$_2$O$_3$ and complexed for 2 hours at 80° C. After cooling, the solution is filtered, the filtrate is ultrafiltered with YM3 (AMICON$^{(R)}$) and the retentate is set at minimum conductivity by alternately adding cation exchanger IR 120 (H$^+$ form) and anion exchanger IRA 410 (OH$^-$ form). Exchanger is filtered out and the filtrate is freeze-dried.

Yield: 1.96 g (70% of theory) of colorless, flocculent powder
H$_2$O content (Karl-Fischer): 7.4%
Gd determination (AAS): 19.9%
MALDI-TOF mass spectrum: molar peak at 25,905 Da (Cld: 25,911 Da)
Elementary analysis (relative to anhydrous substance)
Cld: C 39.35 H 5.15 Gd 21.85 N 13.46
Fnd: C 39.08 H 5.29 Gd 21.03 N 13.68
T$_1$-relaxivity (H$_2$O): 18.0±0.2 [1/mmol. sec]
T$_1$-relaxivity (plasma): 21.5±0.5 [1/mmol. sec] Whole body retention after i.v. application (0.1 mmol Gd/kg body weight; after 14 days; rats): 1.09±0.17% of the dosage. Corresponding Europium-complex: rabbits: 0.23±0.12% of the dosage; mice: 0.46±0.1% of the dosage.

EXAMPLE 2 a) 2-Bromopropionylglycine-benzyl ester 55.9 g (326.1 mmol) of 2-bromopropionic acid chloride is instilled at 0° C. in 100 g (296.4 mmol) of glycine benzyl ester-p-toluenesulfonic acid salt and 33.0 g (326.1 mmol) of triethylamine in 400 ml of methylene chloride. The temperature is not allowed to exceed 5° C. After addition is completed, it is stirred for 1 hour at 0° C., then for 2 hours at room temperature. 500 ml of ice water is added and the water phase is set at pH 2 with 10% aqueous hydrochloric acid. The organic phase is separated, washed once with 300 ml of 5% aqueous soda solution and 400 ml of water. The organic phase is dried on magnesium sulfate and evaporated to dryness in a vacuum. The residue is recrystallized from diisopropyl ether.

Yield: 68.51 g (75w of theory) of a colorless crystalline powder

Elementary analysis
Cld: C 46.76 H 7.19 N 4.54 Br 25.92
Fnd: C 46.91 H 7.28 N 4.45 Br 25.81 b) 1-[4-(Benzyloxycarbonyl)-1-methyl-2-oxo-3-azabutyl]-1,4,7,10-tetraazacyclododecane 50 g (162.2 mmol) of the title compound of Example 2a is added to 55.8 g (324.4 mmol) of 1,4,7,10-tetraazacyclododecane, dissolved in 600 ml of chloroform, and stirred overnight at room temperature. 500 ml of water is added, the organic phase is separated and washed twice each with 400 ml of water. The organic phase is dried on magnesium sulfate and evaporated to dryness in a vacuum. The residue is chromatographed on silica gel (mobile solvent: chloroform/methanol/aqueous 25% ammonia=10:5:1).

Yield: 40.0 g (63% of theory relative to the 2a used) of a slightly yellowish viscous oil Elementary analysis
Cld: C 61.36 H 8.50 N 17.89
Fnd: C 61.54 H 8.68 N 17.68 c) 1-[4-(Benzyloxycarbonyl)-l-methyl-2-oxo-3-azabutyl]-4,7,10-tris(tert-butoxycarbonylmethyl)-1,4,7,10-tetraazacyclododecane (sodium bromide complex)

33 g (169 mmol) of bromoacetic acid-tert-butyl ester is added to 20 g (51.08 mmol) of the title compound of Example 2b and 17.91 (169 mmol) of sodium carbonate in 300 ml of acetonitrile, and it is stirred for 24 hours at 60° C. It is cooled off to 0° C., the salts are filtered out, and the filtrate is evaporated to dryness. The residue is chromatographed on silica gel (mobile solvent: ethyl acetate/ethanol: 15:1). The fractions that contain the product are concentrated by evaporation, and the residue recrystallizes from diisopropyl ether.

Yield: 34.62 g (81% of theory) of a colorless crystalline powder

Elementary analysis
Cld: C 54.54 H 7.59 N 8.37 Na 2.74 Br 9.56
Fnd: C 54.70 H 7.65 N 8.24 Na 2.60 Br 9.37 d) 1-(4-Carboxy-l-methyl-2-oxo-3-azabutyl)-4,7,10-tris(tert-butoxycarbonylmethyl)-1,4,7,10-tetraazacyclododecane (sodium bromide complex)

30 g (35.85 mmol) of the title compound of Example 2c is dissolved in 500 ml of isopropanol and 3 g of palladium catalyst (10% Pd/C) is added. It is hydrogenated overnight at room temperature. Catalyst is filtered out, the filtrate is evaporated to dryness in a vacuum and recrystallized from acetone.

Yield: 22.75 g (85% of theory) of a colorless crystalline powder

Elementary analysis
Cld: C 49.86 H 7.69 N 9.38 Na 3.07 Br 10.71
Fnd: C 49.75 H 7.81 N 9.25 Na 2.94 Br 10.58 e) 1- [4- (4-Nitrophenoxycarbonyl)-1-methyl-2-oxo-3-azabutyl]-4,7,10-tris(tert-butoxy-carbonylmethyl)-1,4,7,10-tetraazacyclododecane (sodium bromide complex)

37.39 (50 mmol) of the carboxylic acid described in Example 2d above is mixed in 500 ml of dichloromethane with 7.6 g (55 mmol) of 4-nitrophenol and cooled to 0° C. After adding 10.8 g (52.5 mmol) of dicyclohexylcarbodiimide, it is stirred overnight at room temperature, then suctioned off from precipitated dicyclohexylurea with renewed cooling, and the filtrate is evaporated to dryness in a vacuum. The residue is recrystallized from ethyl acetate.

Yield: 40.3 g (92.9% of theory) of slightly yellowish powder

Elementary analysis
Cld: C 51.21 H 6.97 N 9.68 Na 2.65 Br 9.21
Fnd: C 51.06 H 7.07 N 9.82 Na 2.40 Br 8.77 f) 36mer-N-(5-DO3A-yl-4-oxo-3-azahexanoyl)-cascade polyamide based on the 36mer-polyamine described in Example 1f 1.84 g (0.2 mmol) of the 36mer-benzyloxycarbonylamine described in Example 1f is dissolved in glacial acetic acid and mixed with 33% hydrogen bromide in glacial acetic acid while being stirred. After 5 hours, the incipient precipitation is completed with diethyl ether, the 36mer-amine-hydrobromide produced is washed with ether, dried in a vacuum and reacted without further purification.

Yield: 1.5 (quantitative)

1.5 g of the above-described 36mer amine-hydrobromide in 100 ml of DMF is mixed with 17.4 g (20 mmol) of the p-nitrophenyl-activated ester described in Example 2e. Within one hour, a solution of 5.05 g (50 mmol) of triethylamine in 20 ml of DMF is then instilled slowly, so that the precipitate forming at the beginning can again dissolve. It is stirred overnight at 45° C., then the solution is concentrated by evaporation in a vacuum, the residue is dissolved at 0° C. in trifluoroacetic acid and stirred overnight at room temperature. It is concentrated by evaporation in a vacuum, the residue is stirred up with diethyl ether, the precipitate is suctioned off and dried in a vacuum. The acid crude product is ultimately dissolved in water, set at pH 7 with diluted sodium hydroxide solution and ultrafiltered with an AMICON$^{(R)}$ YM-3 membrane. The retentate is freeze-dried.

Yield: 4.0 g (78% of theory)

$H_2O$ content (Karl-Fischer): 9.3%

Elementary analysis (relative to anhydrous substance)
Cld: C 45.74 H 6.05 N 15.01 Na 10.68
Fnd: C 45.84 H 5.93 N 15.22 Na 10.20 g) 36mer-Gd Complex of the ligand described in the example above 2.5 g (0.1 mmol) of the sodium salt of the complexing agent acid described in Example 2f above is acidified in water with 5 ml of glacial acetic acid, mixed with 725 mg (2 mmol) of $Gd_2O_3$ and complexed for 2 hours at 80° C. After cooling, the solution is filtered, the filtrate is ultrafiltered with YM3 (AMICON$^{(R)}$) and the retentate is set at minimum conductivity by alternately adding cation exchanger IR 120 ($H^+$ form) and anion exchanger IRA 410 ($OH^-$ form). Exchanger is filtered out, and the filtrate is freeze-dried.

Yield: 2.14 g (74% of theory) of colorless, flocculent powder $H_2O$ content (Karl-Fischer): 8.7%
Gd determination (AAS): 19.4%
MALDI-TOF mass spectrum: molar peak at 26.426 Da (Cld: 26.416 Da)

Elementary analysis (relative to anhydrous substance)
Cld: C 40.24 H 5.32 Gd 21.43 N 13.20
Fnd: C 39.97 H 5.50 Gd 21.19 N 13.32

$T_1$-relaxivity ($H_2O$) : 17.5±0.1 [1/mmol.sec]
$T_1$-relaxivity (plasma): 18.2±0.2 [1/mmol.sec]Whole body retention after i.v. application (0.1 mmol Gd/kg body weight; after 14 days; rats): 1.74±0.22% of the dosage. Corresponding Eu-complex: rabbits: 0.32±0.16% of the dosage; mice: 1.0±0.1% of the dosage.

EXAMPLE 3 a) 1,4,7-Tris(N-benzyloxycarbonylglycyl)-1,4,7,10-tetraazacyclododecane 29.37 g (95.9 mmol) of Z-glycine-N-hydroxysuccinimide ester and 5 g (29 mmol) of cyclene (=1,4,7,10-tetraazacyclododecane) are dissolved in a mixture of 100 ml of toluene/50 ml of dioxane. 9.7 g (95.9 mmol) of triethylamine is added and heated for 12 hours to 70° C. It is evaporated to dryness, the residue is taken up in 400 ml of dichloromethane and extracted 3 times with 200 ml of 5% aqueous potassium carbonate solution each. The organic phase is dried on magnesium sulfate and evaporated to dryness in a vacuum. The residue is chromatographed on silica gel (mobile solvent: ethyl acetate/ethanol=15:1).

Yield: 17.52 g (81% of theory) of a colorless solid
Elementary analysis
Cld: C 61.20 H 6.35 N 13.15
Fnd: C 61.07 H 6.45 N 13.01 b) 1-(Carboxymethoxyacetyl)-4,7,10-tris(N-benzyloxycarbonylglycyl)-1,4,7,10-tetraazacyclododecane 3.97 g (34.19 mmol) of diglycolic anhydride and 6.92 g (68.38 mmol) of triethylamine are added to 17 g (22.79 mmol) of the title compound of Example 3a (dissolved in 100 ml of tetrahydrofuran). It is heated for 6 hours to 50° C. The solution is evaporated to dryness in a vacuum, taken up with 250 ml of dichloromethane and extracted twice with 100 ml of 5% aqueous hydrochloric acid each. The organic phase is dried on magnesium sulfate, evaporated to dryness in a vacuum and the residue is chromatographed on silica gel (mobile solvent: dichloromethane/methanol=20:1).

Yield: 17.48 g (89% of theory) of a colorless solid
Elementary analysis
Cld: C 58.53 H 5.96 N 11.38
Fnd: C 58.37 H 5.81 N 11.45 c) Bis[2-($N_\alpha,N_\varepsilon$-dibenzyloxycarbonyl-lysylamino)-ethyl]-amine 1.03 g (10 mmol) of diethylenetriamine is dissolved in 100 ml of THF, mixed with 2.02 g (2.77 ml, 20 mmol) of triethylamine and 11.25 g (21 mmol) of N,N'-dibenzyloxycarbonyl-lysine-p-nitro-phenylester [O. W. Lever et al., J. Heterocyclic Chem., 23, 901–903 (1986)] and stirred for 3 hours at room temperature. The thick suspension produced is filled up with ether to 250 ml, stirred overnight at room temperature, the voluminous precipitate is suctioned off and washed with 100 ml of THF/ether (1:1) and then again with ether. After drying in a vacuum at 40° C., 8.7 g (97.1% of theory) of colorless powder is obtained.

Elementary analysis
Cld: C 64.34 H 6.86 N 10.94
Fnd: C 64.20 H 6.97 N 10.81 d) N,N,N',N',N'',N''-Hexakis[2-($N_\alpha,N_\varepsilon$-dibenzyloxycarbonyl-lysylamino)-ethyl]-trimesic acid triamide 1.43 g (1.6 mmol) of bis[2-($N_\alpha,N_\varepsilon$-dibenzyloxycarbonyl-lysylamino)-ethyl]-amine in 20 ml of DMF is mixed at 0° C. with 1.39 ml (1.01 g, 10 mmol) of triethylamine and 0.11 g (0.4 mmol) of trimesic acid trichloride (Aldrich) and stirred for 2 hours in ice and overnight at room temperature. It is then concentrated by evaporation in a vacuum, taken up in ethyl acetate and washed with diluted sodium hydroxide solution, 1M hydrochloric acid and semi-saturated NaCl solution and dried on sodium sulfate. After activated carbon is added, it is filtered out with a teflon membrane filter, the filtrate is concentrated by evaporation (1.5 g), dissolved again in about 5 ml of ethyl acetate and chromatographed on silica gel with ethyl acetate/methanol (18:2).

Yield: 0.9 g (79.1%) of colorless powder
Elementary analysis
Cld: C 64.61 H 6.48 N 10.34
Fnd: C 64.45 H 6.60 N 10.28 e) Completely protected benzyloxycarbonyl-36mer-polyamine, synthesized from N,N,N',N',N'',N''-hexakis[2-(lysylamino)-ethyl]-trimesic acid-triamide-core and twelve amine-protected triamine-monocarboxylic acids described in Example 3b 2.84 g (1 mmol) of the 12mer-benzyloxycarbonylamine described in Example 3d above is dissolved in glacial acetic acid and mixed with 33% hydrogen bromide in glacial acetic acid while being stirred. After 3 hours, the incipient precipitation is completed with diethyl ether, the 12mer-amine-hydrobromide produced is washed with ether, dried in a vacuum, and used without further purification in the reaction further described below.

Yield: 2.2 g (quantitative)

17.2 g (20 mmol) of the cyclene-carboxylic acid described in Example 3b, 3.0 g (20 mmol) of 1-hydroxybenzotriazole and 6.4 g (20 mmol) of 2-(1H-benzotriazol-1-yl)-1,1,3,3-tetramethyl-uronium tetrafluoroborate (TBTU; Peboc Limited, UK) are dissolved in DMF and stirred for 15 minutes. The solution is then mixed with 10.3 ml (60 mmol) of N-ethyldiisopropylamine and with 2.2 g (1 mmol) of the above-described 12mer-amine-hydrobromide and stirred overnight at room temperature. After the reaction is completed, it is concentrated by evaporation in a vacuum, and the residue is chromatographed on silica gel with dichloromethane/methanol (17:3).

Yield: 9.6 g (84.5% of theory) of colorless powder
Elementary analysis
Cld: C 59.31 H 6.20 N 12.94
Fnd: C 59.20 H 6.03 N 13.19
MALDI-TOF mass spectrum: molar peak at 11,384 ($M+Na^+$)

f) 36mer-N-(5-DO3A-yl-4-oxo-3-azapentanoyl)-cascade polyamide based on the 36mer polyamine described in Example 3e 2.27 (0.2 mmol) of the 36mer-benzyloxycarbonylamine described in Example 3e is dissolved in glacial acetic acid and mixed with 33% hydrogen bromide in glacial acetic acid while being stirred. After 5 hours, the incipient precipitation is completed with diethyl ether, the 36mer-amine-hydrobromide produced is washed with ether, dried in a vacuum and used without further purification in the reaction further described below.

Yield: 1.9 g (quantitative)

14.7 g (20 mmol) of the carboxylic acid described in Example 1i, 3.0 g (20 mmol) of 1-hydroxybenzotriazole and 6.4 g (20 mmol) of 2-(1H-benzotriazol-1-yl)-1,1,3,3-tetramethyluronium tetrafluoroborate (TBTU; Peboc Limited, UK) are dissolved in DMF and stirred for 15 minutes. The solution is then mixed with 10.3 ml (60 mmol) of N-ethyldiisopropylamine and with 1.9 g (0.2 mmol) of the above-described 36mer-amine-hydrobromide and stirred for 4 days at room temperature. After the reaction is completed, it is concentrated by evaporation in a vacuum, the residue is dissolved at 0° C. in trifluoroacetic acid, stirred overnight at room temperature, concentrated by evaporation in a vacuum and the residue is stirred up with ether. The substance is suctioned off, washed with ether, dried in a vacuum, ultimately dissolved in water, set at pH 7 with 2N sodium hydroxide solution and the solution is purified with an Amicon$^{(R)}$-ultrafiltration membrane YM 3 (cut off: 3000 Da). The retentate is then filtered and freeze-dried.

Yield: 3.93 g (75% of theory) of flocculent powder
$H_2O$ content (Karl-Fischer): 5.0%

Elementary analysis (relative to anhydrous substance)
Cld: C 44.48 H 5.75 N 16.05 Na 9.98
Fnd: C 44.77 H 5.91 N 15.96 Na 9.50 g) 36mer-Gd Complex of the ligand described in Example 3f above 2.6 g (0.1 mmol) of the sodium salt of the complexing agent acid described in Example 3f above is acidified in water with 5 ml of glacial acetic acid, mixed with 725 mg (2 mmol) of $Gd_2O_3$ and complexed for 2 hours at 80° C. After cooling, the solution is filtered, the filtrate is ultrafiltered with YM3 (AMICON$^{(R)}$) and the retentate is set at minimum conductivity by alternately adding cation exchanger IR 120 ($H^+$ form) and anion exchanger IRA 410 ($OH^-$ form). Exchanger is filtered out and the filtrate is freeze-dried.

Yield: 2.22 g (72% of theory) of colorless, flocculent powder
$H_2O$ content (Karl-Fischer): 8.9%
Gd determination (AAS): 18.5%
MALDI-TOF mass spectrum: molar peak at 28,058 Da (Cld: 28,049 Da)
Elementary analysis (relative to anhydrous substance)
Cld: C 39.44 H 5.10 Gd 20.18 N 14.23
Fnd: C 39.56 H 5.26 Gd 19.88 N 14.09

EXAMPLE 4 a) 36mer-N-(5-DO3A-yl-4-oxo-3-azahexanoyl)-cascade polyamide based on the 36mer polyamine described in Example 3e 2.27 g (0.2 mmol) of the 36mer-benzyloxycarbonylamine described in Example 3e is dissolved in glacial acetic acid and mixed with 33% hydrogen bromide in glacial acetic acid while being stirred. After 5hours, the incipient precipitation is completed with diethyl ether, the 36mer-amine-hydrobromide produced is washed with ether, dried in a vacuum and further reacted without further purification.

Yield: 1.9 g (quantitative)

1.9 g of the above-described 36mer amine-hydrobromide in 100 ml of DMF is mixed with 17.4 g (20 mmol) of the p-nitrophenyl-activated ester described in Example 2e. Within one hour, a solution of 5.05 g (50 mmol) of triethylamine in 20 ml of DMF is then slowly instilled, so that the precipitate forming at the beginning can again dissolve. It is stirred overnight at 45° C., then the solution is concentrated by evaporation in a vacuum, the residue is dissolved at 0° C. in trifluoroacetic acid and stirred overnight at room temperature. It is concentrated by evaporation in a vacuum, the residue is stirred up with diethyl ether, the precipitate is suctioned off and dried in a vacuum. The acid crude product is ultimately dissolved in water, set at pH 7 with diluted sodium hydroxide solution and ultrafiltered with an AMICON$^{(R)}$ YM-3 membrane. The retentate is freeze-dried.

Yield: 4.0 g (72.9% of theory)
$H_2O$ content (Karl-Fischer): 7.5%
Elementary analysis (relative to anhydrous substance)
Cld: C 45.30 H 5.92 N 15.73 Na 9.78
Fnd: C 45.56 H 6.10 N 15.65 Na 9.47 b) 36mer-Gd Complex of the ligand described in Example 4a above 2.74 g (0.1 mmol) of the sodium salt of the complexing agent acid described in Example 4a above is acidified in water with 5 ml of glacial acetic acid, mixed with 725 mg (2 mmol) of $Gd_2O_3$ and complexed for 2 hours at 80° C. After cooling, the solution is filtered, the filtrate is ultrafiltered with YM3 (AMICON$^{(R)}$) and the retentate is set at minimum conductivity by alternately adding cation exchanger IR 120 ($H^+$ form) and anion exchanger IRA 410 ($OH^-$ form). Exchanger is filtered out and the filtrate is freeze-dried.

Yield: 2.46 g (77.8% of theory) of colorless, flocculent powder
$H_2O$ content (Karl-Fischer): 9.7%
Gd determination (AAS): 18.1%
MALDI-TOF mass spectrum: molar peak at 28,563 Da (Cld: 28.554 Da)
Elementary analysis (relative to anhydrous substance)
Cld: C 40.26 H 5.26 Gd 19.83 N 13.98
Fnd: C 40.01 H 5.40 Gd 19.68 N 14.11

EXAMPLE 5 a) 1,7-Bis(benzyloxycarbonyl)-4-hydroxysuccinyl-1,4,7-triazaheptane 20.20 g (201.9 mmol) of succinic anhydride and 40.86 g (403.8 mmol) of triethylamine are added to 50 g (134.6 mmol) of 1,7-bis(benzyloxycarbonyl)-1,4,7-triazaheptane (Example 1d) in 500 ml of tetrahydrofuran and stirred overnight at 40° C. It is evaporated to dryness, the residue is taken up in 1000 ml of dichloromethane and washed twice with 500 ml of 5% hydrochloric acid each. The organic phase is dried on magnesium sulfate and evaporated to dryness. The residue is chromatographed on silica gel (mobile solvent=dichloromethane/methanol: 20:1).

Yield: 56.0 g (93% of theory) of a colorless solid
Elementary analysis
Cld: C 59.05 H 6.53 N 9.39
Fnd: C 59.17 H 6.69 N 9.27 b) N-Hydroxysuccinimide ester of 1,7-bis(benzyloxycarbonyl)-4-hydroxysuccinyl-1,4,7-triazaheptane 14.4 g (125.14 mmol) of N-hydroxysuccinimide is added to 56 g (125.14 mmol) of the title compound of Example 5a in 300 ml of dichloromethane. It is cooled to 0° C. and 28.4 g (137.66 mmol) of dicyclohexylcarbodiimide is added. Then, it is stirred for 6 hours at room temperature. Precipitated solid is filtered out, and the filtrate is evaporated to dryness in a vacuum. The residue is recrystallized from ether/2-propanol.

Yield: 62.01 g (91% of theory) of a crystalline colorless solid
Elementary analysis
Cld: C 57.35 H 5.92 N 10.29
Fnd: C 57.24 H 5.99 N 10.12 c) 11,4,7-Tris{7-benzyloxycarbonylamino-5-[2-(benzyloxycarbonylamino)-ethyl]-4-oxo-5-azaheptanoyl}1,4,7,10-tetraazacyclododecane 52.22 g (95.9 mmol) of the title compound of Example 5b and 5 g (29 mmol) of cyclene (=1,4,7,10-tetraazacyclododecane) are dissolved in a mixture of 200 ml of toluene/100 ml of dioxane. 9.7 g (95.9 mmol) of triethylamine is added and heated for 12 hours to 70° C. It is evaporated to dryness, the residue is taken up in 600 ml of dichloromethane and extracted three times with 300 ml of 5% aqueous potassium carbonate solution each. The organic phase is dried on magnesium sulfate and evaporated to dryness in a vacuum. The residue is chromatographed on silica gel (mobile solvent: ethyl acetate/ethanol=15:1).

Yield: 28.95 g (69% of theory) of a colorless solid
Elementary analysis
Cld: C 61.44 H 7.04 N 11.62
Fnd: C 61.57 H 6.91 N 11.69 d) 1,4,7-Tris-{7-benzyloxycarbonylamino-5-[2-(benzyloxycarbonylamino)-ethyl]-4-oxo-5-azaheptanoyl}-10-hydroxysuccinyl-1,4,7,10-tetraazacyclododecane 2.90 g (29 mmol) of succinic anhydride and 5.87 g (58 mmol) of triethylamine are added to 28 g (19.35 mmol) of the title compound of Example 5c, dissolved in tetrahydrofuran. It is heated for 6 hours to 50° C. The solution is evaporated to dryness in a vacuum, taken up with 200 ml of dichloromethane and extracted twice with 100 ml of 5% aqueous hydrochloric acid each. The organic phase is dried on magnesium sulfate, evaporated to dryness in a vacuum, and the residue is chromatographed on silica gel (mobile solvent: dichloromethane/methanol=20:1).

Yield: 26.94 g (90% of theory) of a colorless solid
Elementary analysis
Cld: C 60.57 H 6.84 N 10.87
Fnd: C 60.41 H 6.95 N 10.75 e) 1,4,7,10,13,16-Hexakis[N-benzyloxycarbonyl-β-alanyl]-1,4,7,10,13,16-hexaazacyclooctadecane 516 mg (2 mmol) of 1,4,7,10,13,16-hexaazacyclooctadecane (hexacyclene; Fluka) is azeotropically dehydrated with toluene. A solution of 3.35 g (15 mmol) of benzyloxycarbonyl-β-alanine (Sigma) in tetrahydrofuran (THF) as well as 3.71 g (15 mmol) of 2-ethoxy-1-ethoxycarbonyl-1,2-dihydroquinoline (EEDQ; Fluka) are added to the cooled solution of hexacyclene in toluene at room temperature and stirred overnight. After the reaction is completed, the product is precipitated by adding hexane, and the precipitate is chromatographed on silica gel with dichloromethane/hexane/isopropanol (20:10:1).

Yield: 2.06 g (69w of theory)
Elementary analysis
Cld: C 62.89 H 6.50 N 11.28
Fnd: C 62.74 H 6.32 N 11.50 f) Completely protected benzyloxycarbonyl-36mer-polyamine, synthesized from 1,4,7,10,13,16-hexakis(β-alanyl)-1,4,7,10,13,16-hexaazacyclooctadecane-core and six amine-protected hexaamine-monocarboxylic acids described in Example 5d 1.49 g (1 mmol) of the hexa-benzyloxycarbonylamine described in Example 5e above is dissolved in glacial acetic acid and mixed with 33% hydrogen bromide in glacial acetic acid while being stirred. After 60 minutes, the incipient precipitation is completed with diethyl ether, the hexamine-hydrobromide produced is washed with ether, dried in a vacuum and used without further purification in the reaction further described below.

Yield: 1.2 g (quantitative)

7.0 g (7.5 mmol) of the amine-protected hexa-amine-monocarboxylic acid described in Example 5d, 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 1.2 g (1 mmol) of the above-described hexa-amine-hydrobromide and stirred overnight at room temperature. After the reaction is completed, it is concentrated by evaporation in a vacuum and the residue is chromatographed on silica gel with dichloromethane/methanol (17:3).

Yield: 8.5 g (82% of theory) of a colorless powder
Elementary analysis
Cld: C 61.83 H 6.59 N 12.15
Fnd: C 61.59 H 6.71 N 12.02

MALDI-TOF mass spectrum: molar peak at 10.397 (M+Na$^+$)

g) 36mer-N-(5-DO3A-yl-4-oxo-3-azahexanoyl)-cascade polyamide based on the polyamine described in Example 5e 2.07 g (0.2 mmol) of the 36mer-benzyloxycarbonylamine described in Example 5f is dissolved in glacial acetic acid and mixed with 33% hydrogen bromide in glacial acetic acid while being stirred. After 5 hours, the incipient precipitation is completed with diethyl ether, the 36mer-amine-hydrobromide produced is washed with ether and dried in a vacuum and reacted without further purification.

Yield: 1.7 g (quantitative)

1.7 g of the above-described 36mer amine-hydrobromide in 100 ml of DMF is mixed with 17.4 g (20 mmol) of the p-nitrophenyl-activated ester described in Example 2e. Within one hour, a solution of 5.05 g (50 mmol) of triethylamine in 20 ml of DMF is then slowly instilled, so that the precipitate forming at the beginning can again dissolve. It is stirred overnight at 45° C., then the solution is concentrated by evaporation in a vacuum, the residue is dissolved at 0° C. in trifluoroacetic acid and stirred overnight at room temperature. It is concentrated by evaporation in a vacuum, the residue is stirred up with diethyl ether, the precipitate is suctioned off and dried in a vacuum. The acid crude product is ultimately dissolved in water, set at pH 7 with diluted sodium hydroxide solution and ultrafiltered with an AMICON$^{(R)}$ YM-3 membrane. The retentate is freeze-dried.

Yield: 4.4 g (83% of theory)
H$_2$O content (Karl-Fischer): 7.8%
Elementary analysis (relative to anhydrous substance)
Cld: C 45.80 H 6.08 N 15.51 Na 10.18
Fnd: C 45.88 H 6.23 N 15.66 Na 9.70 h) 36mer-Gd complex of the ligand described in Example 5g above 2.65 g (0.1 mmol) of the sodium salt of the complexing agent acid described in Example 5g above is acidified in water with 5 ml of glacial acetic acid, mixed with 725 mg (2 mmol) of Gd$_2$O$_3$ and complexed for 2 hours at 80° C. After cooling, the solution is filtered, the filtrate is ultrafiltered with YM3 (AMICON$^{(R)}$) and the retentate is set at minimum conductivity by alternately adding cation exchanger IR 120 (H$^+$ form) and anion exchanger IRA 410 (OH$^-$ form). Exchanger is filtered out and the filtrate is freeze-dried.

Yield: 2.41 g (81% of theory) of colorless, flocculent powder
H$_2$O content (Karl-Fischer): 7.5%
Gd determination (AAS): 18.7%
MALDI-TOF mass spectrum: molar peak at 27,580 Da (Cld: 27,566 Da)
Elementary analysis (relative to anhydrous substance)
Cld: C 40.52 H 5.37 Gd 20.54 N 13.72
Fnd: C 40.30 H 5.50 Gd 20.11 N 13.56

EXAMPLE 6

36 mer-Gd-DTPA-monoamide based on the 36mer-polyamine described in Example 5f 1.04 g (0.2 mmol) of the 36mer-poly-benzyloxycarbonylamine described in Example 5f is dissolved in glacial acetic acid and mixed with 33% hydrogen bromide in glacial acetic acid while being stirred. After 3 hours, the incipient precipitation is completed with diethyl ether, the 36mer-amine-hydrobromide produced is washed with ether and dried in a vacuum. The residue is then taken up in water and set at pH 9.5 by adding 1N sodium hydroxide solution. 4.35 g (10.8 mmol) of N$^3$-(2,6-dioxomorpholinoethyl)-N$^6$-(ethoxycarbonylmethyl)-3,6-diazaoctanedioic acid (Example 13a of EP 0331 616) is added in solid form to this solution, and the pH is kept constant at 9.5 by further addition of sodium hydroxide solution. After the addition is completed, a pH>13 is set to saponify the DTPA-ethyl ester with 5N sodium hydroxide solution, and it is stirred overnight at room temperature. Then, it is set at pH 5 with concentrated hydrochloric acid, mixed with 1.96 g (5.4 mmol) of Gd$_2$O$_3$, stirred for 30 minutes at 80° C., set at pH 7 after the cooling and desalted with a YM3 AMICON-ultrafiltration membrane. The retentate is ultimately membrane-filtered and freeze-dried.

Yield: 2.85 g (92.4% of theory)

H$_2$O content (Karl-Fischer): 9.0%
Gd determination (AAS): 20.3%
Elementary analysis (relative to anhydrous substance)
Cld: C 35.46 H 4.26 Gd 22.29 N 10.92 Na 3.26
Fnd: C 35.18 H 4.44 Gd 21.75 N 10.83 Na 3.59

EXAMPLE 7 a) 5-Benzyloxycarbonylamino-2-[3-(benzyloxycarbonylamino)-propyl]-valeric acid 24.48 g (143.5 mmol) of benzyl chloroformate and 5N aqueous sodium hydroxide solution are simultaneously instilled at 0° C. in 10 g (57.39 mmol) of 4-carboxy-1,7-diaminoheptahe (produced according to: A. Reissert, Chem. Ber. 26, 2137 (1893); 27, 979 (1894)) in 150 ml of water, and the pH is kept at 10. It is stirred overnight at room temperature. It is extracted twice with 150 ml of ethyl acetate each. The water phase is carefully acidified with 4N aqueous hydrochloric acid (pH 2) and extracted three times with 200 ml of ethyl acetate each. The organic phase is dried on magnesium sulfate and evaporated to dryness in a vacuum.

Yield: 24.13 g (95% of theory) of a vitreous solid
Elementary analysis
Cld: C 59.05 H 6.53 N 9.39
Fnd: C 59.19 H 6.71 N 9.18 b) 5-Benzyloxycarbonylamino-2-[3-(benzyloxycarbonylamino)-propyl]-valeric acid-N-hydroxysuccinimide ester 6.24 g (54.24 mmol) of N-hydroxysuccinimide is added to 24 g (54.24 mmol) of the title compound of Example 7a, dissolved in 100 ml of dichloromethane. It is cooled to 0° C. and 12.31 g (59.66 mmol) of dicyclohexylcarbodiimide is added. Then, it is stirred for 6 hours at room temperature. Precipitated solid is filtered out and the filtrate is evaporated to dryness in a vacuum. The residue is recrystallized from ether/2-propanol.

Yield: 27.51 g (94% of theory) of a crystalline, colorless solid
Elementary analysis
Cld: C 62.33 H 6.16 N 7.79
Fnd: C 62.17 H 6.03 N 7.85 c) 1,4,7-Tris{5-benzyloxycarbonylamino-2-[3-(benzyloxycarbonylamino)-propyl]-valeryl}-1,4,7,10-tetraazacyclododecane 27 g (50.04 mmol) of the title compound of Example 7b and 2.61 g (15.16 mmol) of cyclene (=1,4,7,10-tetraazacyclododecane) are dissolved in a mixture of 100 ml of toluene/50 ml of dioxane. 3.07 g (30.32 mmol) of triethyalmine is added and heated for 12 hours to 70° C. It is evaporated to dryness, the residue is taken up in 300 ml of dichloromethane and extracted three times with 150 ml of 5% aqueous potassium carbonate solution each. The organic phase is dried on magnesium sulfate and evaporated to dryness in a vacuum. The residue is chromatographed on silica gel (mobile solvent: ethyl acetate/ethanol=15:1).

Yield: 13.81 g (63% of theory) of a colorless solid
Elementary analysis
Cld: C 66.46 H 7.26 N 9.69
Fnd: C 66.28 H 7.39 N 9.51 d) 1-[Carboxy-methoxyacetyl)-4,7,10-tris{5-benzyloxycarbonylamino-2-[3-benzyloxycarbonylamino)-propyl]-valeryl}-1,4,7,10-tetraazacyclododecane 1.57 g (13.5 mmol) of diglycolic anhydride and 2.73 g (27 mmol) of triethylamine are added to 13 g (9 mmol) of the title compound of Example 7c in 80 ml of tetrahydrofuran. It is heated for 6 hours to 50° C. The solution is evaporated to dryness in a vacuum, taken up with 150 ml of dichloromethane and extracted twice with 100 ml of 5% aqueous hydrochloric acid each. The organic phase is dried on magnesium sulfate, evaporated to dryness in a vacuum, and the residue is chromatographed on silica gel (mobile solvent: dichloromethane/methanol=20:1).

Yield: 12.5 g (89% of theory) of a colorless solid
Elementary analysis
Cld: C 64.60 H 6.97 N 8.97
Fnd: C 64.41 H 6.85 N 8.90 e) Completely protected benzyloxycarbonyl-36mer-polyamine, synthesized from N, N, N',N',N",N"-hexakis(2-aminoethyl)-trimesic acid triamide-core and six amine-protected hexaamine-monocarboxylic acids described in Example 7d 1.27 g (1 mmol) of the hexa-benzyloxycarbonylamine described in Example 1e is dissolved in glacial acetic acid and mixed with 33% hydrogen bromide in glacial acetic acid while being stirred. After 60 minutes, the incipient precipitation is completed with diethyl ether, the hexamine-hydrobromide produced is washed with ether, dried in a vacuum and used without further purification in the reaction further described below.

Yield: 0.95 g (quantitative)

11.7 g (7.5 mmol) of the cyclene-carboxylic acid described in Example 7d, 1.2 g (7.5 mmol) of 1-hydroxybenzotriazole and 2.4 g (7.5 mmol) of 2-(1H-benzotriazol-1-yl)-1,1,3,3-tetramethyl-uronium tetrafluoroborate (TBTU; Peboc Limited, UK) are dissolved in DMF and stirred for 15 minutes. This solution is then mixed with 5.16 ml (30 mmol) of N-ethyldiisopropylamine and with 0.95 g (1 mmol) of the above-described hexa-amine-hydrobromide and stirred overnight at room temperature. After the reaction is completed, it is concentrated by evaporation in a vacuum, and the residue is chromatographed on silica gel with dichloromethane/methanol (17:3).

Yield: 7.40 g (76% of theory) of a colorless powder
Elementary analysis
Cld: C 64.82 H 6.99 N 9.93
Fnd: C 64.58 H 7.11 N 10.04
MALDI-TOF mass spectrum: molar peak at 9751 (M+Na$^+$)

f) 36mer-N-(5-DO3A-yl-4-oxo-3-azahexanoyl)-cascade polyamide based on the polyamine described in Example 7e 1.95 g (0.2 mmol) of the 36mer-benzyloxycarbonylamine described in Example 7e is dissolved in glacial acetic acid and mixed with 33% hydrogen bromide in glacial acetic acid while being stirred. After 5 hours, the incipient precipitation is completed with diethyl ether, the 36mer-amine-hydrobromide produced is washed with ether and dried in a vacuum and reacted without further purification.

Yield: 1.6 g (quantitative)

1.6 g of the above-described 36mer amine-hydrobromide in 100 ml of DMF is mixed with 17.4 g (20 mmol) of the p-nitrophenyl-activated ester described in Example 2e. Within one hour, a solution of 5.05 g (50 mmol) of triethylamine in 20 ml of DMF is then slowly instilled so that precipitate forming at the beginning can again dissolve. It is stirred overnight at 45° C., then the solution is concentrated by evaporation in a vacuum, the residue is dissolved at 0° C. in trifluoroacetic acid and stirred overnight at room temperature. It is concentrated by evaporation in a vacuum, the residue is stirred up with diethyl ether, the precipitate is suctioned off and dried in a vacuum. The acid crude product is ultimately dissolved in water, set at pH 7 with diluted sodium hydroxide solution and ultrafiltered with an AMICOM$^{(R)}$ YM-3 membrane. The retentate is freeze-dried.

Yield: 3.9 g (76% of theory)

H$_2$O content (Karl-Fischer): 8.0%
Elementary analysis (relative to anhydrous substance)
Cld: C 46.59 H 6.23 N 14.69 Na 10.46
Fnd: C 46.82 H 6.47 N 14.55 Na 10.19 g) 36mer-Gd complex of the ligand described in the example above 2.58 g (0.1 mmol) of the sodium salt of the complexing agent acid described in Example 7f above is acidified in water with 5 ml of glacial acetic acid, mixed with 725 mg (2 mmol) of Gd$_2$O$_3$ and complexed for 2 hours at 80° C. After cooling, the solution is filtered, the filtrate is ultrafiltered with YM3 (AMICOM$^{(R)}$) and the retentate is set at minimum conductivity by alternately adding cation exchanger IR 120 (H$^+$form) and anion exchanger IRA 410 (OH$^-$form). Exchanger is filtered out, and the filtrate is freeze-dried.

Yield: 2.08 g (72% of theory) of colorless, flocculent powder

H$_2$O content (Karl-Fischer): 7.0%
Gd determination (AAS): 19.3%
MALDI-TOF mass spectrum: molar peak at 26,915 Da (Cld: 26,921 Da)
Elementary analysis (relative to anhydrous substance)
Cld: C 41.09 H 5.49 Gd 21.03 N 12.96
Fnd: C 41.20 H 5.60 Gd 20.66 N 13.19

EXAMPLE 8 a) 3,5-Bis[4-(benzyloxycarbonyl)-2-oxo-1,4-diazabutyl]-benzoic acid 123.8 g (404.2 mmol) of N-Z-glycine-N-hydroxysuccinimide ester is added to 30 g (197.17 mmol) of 3,5-diaminobenzoic acid in 600 ml of dichloromethane. At 0° C., 60.7 g (800 mmol) of triethylamine, dissolved in 100 ml of dichloromethane, is instilled within 5 minutes, and it is stirred overnight at room temperature. It is extracted three times with 500 ml of 10% hydrochloric acid each, the organic phase is dried on magnesium sulfate and evaporated to dryness in a vacuum. The residue is recrystallized from acetone.

Yield: 97.87 g (95% of theory) of a colorless, crystalline solid
Elementary analysis
Cld: C 59.77 H 5.02 N 10.72
Fnd: C 59.65 H 5.17 N 10.59 b) 3,5-Bis[4-(benzyloxycarbonyl-2-oxo-1,4-diazabutyl]-benzoic acid-N-hydroxysuccinimide ester 13.21 g (114.8 mmol) of N-hydroxysuccinimide is added to 60 g (114.8 mmol) of the title compound of Example 8a, dissolved in 300 ml of dichloromethane. It is cooled to 0° C. and 26.06 g (126.3 mmol) of dicyclohexylcarbodiimide is added. Then, it is stirred for 6 hours at room temperature. Precipitated solid is filtered out, and the filtrate is evaporated to dryness in a vacuum. The residue is recrystallized from ether/2-propanol.

Yield: 65.44 g (92% of theory) of a crystalline, colorless solid
Elementary analysis
Cld: C 58.16 H 4.72 N 11.30
Fnd: C 58.31 H 4.90 N 11.15 c) 1,4,7-Tris{3,5-bis-[4-benzyloxycarbonyl-2-oxo-1,4-diazabutyl]-benzoyl}-1,4,7,10-tetraazacyclododecane 60 g (96.84 mmol) of the title compound of Example 8b and 5.05 g (29.34 mmol) of cyclene (=1,4,7,10-tetraazacyclododecane) are dissolved in a mixture of 200 ml of toluene/100 ml of dioxane. 5.94 g (58.68 mmol) of triethylamine is added and heated for 12 hours to 70° C. It is evaporated to dryness, the residue is taken up in 600 ml of dichloromethane and extracted three times with 300 ml of 5% aqueous potassium carbonate solution each. The organic phase is dried on magnesium sulfate and evaporated to dryness in a vacuum. The residue is chromatographed on silica gel (mobile solvent: ethyl acetate/ethanol=15:1).

Yield: 31.65 g (64% of theory) of a colorless solid
Elementary analysis
Cld: C 61.27 H 5.50 N 13.29
Fnd: C 61.15 H 5.61 N 13.10 d) 1-(Carboxymethoxyacetyl)-4,7,10-tris{3,5-bis-[4-benzyloxycarbonyl-2-oxo-1,4-diazabutyl]-benzoyl}-1,4,7,10-tetraazacyclododecane 3.1 g (26.7 mmol) of diglycolic anhydride and 5.4 g (53.4 mmol) of triethylamine are added to 30 g (17.8 mmol) of the title compound of Example 8c, dissolved in 150 ml of tetrahydrofuran. It is heated for 6 hours to 50° C. The solution is evaporated to dryness in a vacuum, taken up with 250 ml of dichloromethane and extracted twice with 150 ml of 5% aqueous hydrochloric acid each. The organic phase is dried on magnesium sulfate, evaporated to dryness in a vacuum, and the residue is chromatographed on silica gel (mobile solvent: dichloromethane/methanol=2Q:1).

Yield: 29.83 g (93% of theory) of a colorless solid
Elementary analysis
Cld: C 59.99 H 5.37 N 12.44
Fnd: C 59.81 H 5.45 N 12.29 e) Completely protected benzyloxycarbonyl-36mer-polyamine, synthesized from N, N, N',N',N'',N''-hexakis(2-aminoethyl)-trimesic acid triamide-core and six amine-protected hexaamine-monocarboxylic acids described in Example 8d 1.27 g (1 mmol) of the hexa-benzyloxycarbonylamine described in Example 1e above is dissolved in glacial acetic acid and mixed with 33% hydrogen bromide in glacial acetic acid while being stirred. After 60 minutes, the incipient precipitation is completed with diethyl ether, the hexamine-hydrobromide produced is washed with ether, dried in a vacuum and used without further purification in the reaction further described below.

Yield: 0.95 g (quantitative)

13.5 g (7.5 mmol) of the cyclene-carboxylic acid described in Example 8d above, 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and mixed with 0.95 g (1 mmol) of the above-described hexaaminehydrobromide and stirred overnight at room temperature. After the reaction is completed, it is concentrated by evaporation in a vacuum, and the residue is chromatographed on silica gel with dichloromethane/methanol (8:1).

Yield: 8.75 g (81% of theory) of a colorless powder
Elementary analysis
Cld: C 64.34 H 5.62 N 13.61
Fnd: C 64.22 H 5.86 N 13.51
MALDI-TOF mass spectrum: molar peak at 10,832 (M+Na$^+$)

f) 36mer-N-(5-DO3A-yl-4-oxo-3-azahexanoyl)-cascade polyamide based on the polyamine described in Example 8e 2.16 g (0.2 mmol) of the 36mer-benzyloxycarbonylamine described in Example 8e is dissolved in glacial acetic acid and mixed with 33% hydrogen bromide in glacial acetic acid while being stirred. After 5 hours, the incipient precipitation is completed with diethyl ether, the 36mer-amine-hydrobromide produced is washed with ether and dried in a vacuum and reacted without further purification.

Yield: 1.8 g (quantitative)

1.8 g of the above-described 36mer amine-hydrobromide in 100 ml of DMF is mixed with 17.4 g (20 mmol) of the p-nitrophenyl-activated ester described in Example 2e. Within one hour, a solution of 5.05 g (50 mmol) of triethylamine in 20 ml of DMF is then slowly instilled, so that the precipitate forming at the beginning can again dissolve. It is stirred overnight at 45° C., then the solution is concentrated by evaporation in a vacuum, the residue is dissolved at 0° C. in trifluoroacetic acid and stirred overnight at room temperature. It is concentrated by evaporation in a vacuum, the residue is stirred up with diethyl ether, the precipitate is suctioned off and dried in a vacuum. The acid crude product is ultimately dissolved in water, set at pH 7 with diluted sodium hydroxide solution and ultrafiltered with an AMICOM$^{(R)}$ YM-3 membrane. The retentate is freeze-dried.

Yield: 4.6 g (84% of theory)
H$_2$O content (Karl-Fischer): 9.5%
Elementary analysis (relative to anhydrous substance)
Cld: C 47.18 H 5.66 N 16.08 Na 10.00
Fnd: C 47.31 H 5.52 N 16.30 Na 9.57 g) 36mer-Gd complex of the ligand described in the example above 2.74 g (0.1 mmol) of the sodium salt of the complexing agent acid described in Example 8f above is acidified in water with 5 ml of glacial acetic acid, mixed with 725 mg (2 mmol) of Gd$_2$O$_3$ and complexed for 2 hours at 80° C. After cooling, the solution is filtered, the filtrate is ultrafiltered with YM3 (AMICOM$^{(R)}$) and the retentate is set at minimum conductivity by alternately adding cation exchanger IR 120 (H$^+$form) and anion exchanger IRA 410 (OH$^-$form). Exchanger is filtered out, and the filtrate is freeze-dried.

Yield: 2.27 g (74% of theory) of colorless, flocculent powder
H$_2$O content (Karl-Fischer): 8.6%
Gd determination (AAS): 18.2%
MALDI-TOF mass spectrum: molar peak at 27,992 Da (Cld: 28,001 Da)
Elementary analysis (relative to anhydrous substance)
Cld: C 41.82 H 5.02 Gd 20.22 N 14.26
Fnd: C 41.99 H 4.96 Gd 19.87 N 14.40

Example for an In Vivo Comparison with an Extracellular Contrast Medium

The suitability of the compound described in Example 11 as blood-pool-agent is shown in the following test.

As test animals, three male (Schering-SPF) rats that are 200–250 g in weight are used. 0.2 ml (respectively 25 mmol/L) of the following contrast medium solution per animal is administered intravenously: mixture of 1 part each of the compound of 11, named compound 1 below, and the dysprosium complex of 3,6,9-triaza-3,6,9-tris (carboxymethyl)-undecanedioic acid (Dy-DTPA), named compound 2 below. Blood samples are taken with a catheter in the common carotid artery at the following times: 1, 3, 5, 10, 15, 20, 30, 45, 60, 90, 120 minutes p.i. In the blood samples obtained, the concentrations of gadolinium (Gd) and dysprosium (Dy) are measured with the aid of atomic emission spectrometry (ICP-AES) in each case in a parallel manner. The portion of the injected contrast medium of compound 1 (Gd) and compound 2 (Dy, comparison substance), remaining in the blood space, can be compared in the same animals by the different marking. The a- and b-half-lives, the volume of distribution as well as the total clearance can be calculated from the blood concentrations with the aid of special software (Topfit program). These data thus supply indications on compounds remaining in the intravascular space, the ratios of distribution in the organism and the excretion.

Results: Mainly earlier on, considerably higher blood concentrations of compound 1 compared to the extracellular contrast medium (compound 2) are obtained (see FIG. 1).

The considerably higher blood concentrations of compound 1 earlier on (compared to compound 2) point to a considerably lower volume of distribution (see also Vd ss), i.e., compound 1 is not dispersed as compound 2 in the intravascular space (vessels) and in the extracellular space, but for the most part only in the intravascular space. Later on, the blood level drops quickly, however, and the excretion time or β-half-life of compound 1 is considerably shorter than in the case of other blood-pool-agents. The total blood clearance of compound 1 is only somewhat lower compared to compound 2, which can indicate a similarly good renal excretion.

Thus, the compound described in Example 11 has the requirements of a blood-pool agent: efficient excretion from the blood (through the kidneys), but a considerably lower volume of distribution than an extracellular contrast medium.

|  | Compound 1 (Gd) | Compound 2 (Dy) | Unit |
|---|---|---|---|
| α-t$^{1/2}$ | 3.0 ± 0.6 | 1.5 ± 0.5 | min |
| β-t$^{1/2}$ | 36.5 ± 18.2 | 19.2 ± 2.5 | min |
| Vd ss | 0.18 ± 0.07 | 0.41 ± 0.04 | L/kg |
| Total Clearance | 13.6 ± 1.5 | 16.8 ± 0.9 | ml/min*kg |

We claim:

1. Cascade polymer complexes that contain a) complexing ligands of general formula I

$$A\text{—}\{X\text{—}[Y\text{—}(Z\text{—}\{W\text{—}K_W\}_z)_y]_x\}_a \qquad (I)$$

in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, K stands for the radical of a complexing agent, a stands for numbers 2 to 12, x, y, z and w, independently of one another, stand for numbers 1 to 4, provided that at least two reproduction units are different, that $16 \leq a \cdot x \cdot y \cdot z \cdot w \leq 64$ holds true for the product of the multiplicities, and that at least one of cascade reproduction units X, Y, Z, W stands for a 1,4,7,10-tetraazacyclododecane or 1,4,8,11-tetraazacyclotetradecane reproduction unit, b) at least 16 ions of an element of atomic numbers 20 to 29, 39, 42, 44 or 57–83, c) optionally cations of inorganic and/or organic bases, amino acids or amino acid amides as well as d) optionally acylated terminal amino groups.

2. Cascade polymer complexes according to claim 1, characterized in that A means a nitrogen atom,

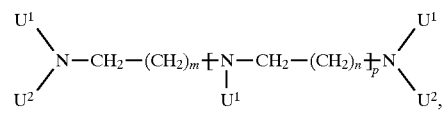

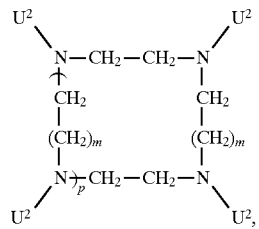

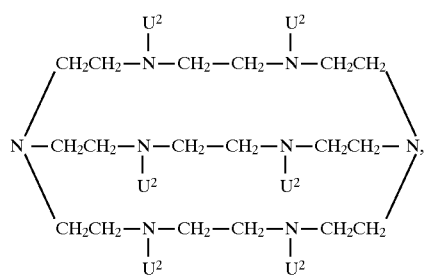

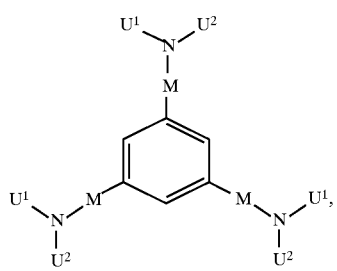

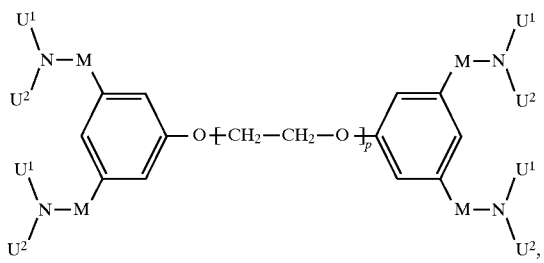

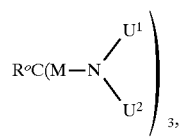

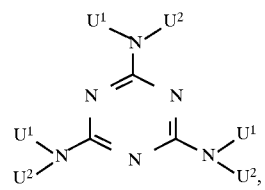

or

-continued

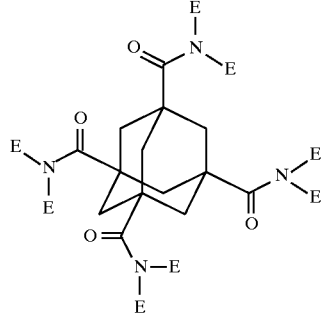

in which m and n stand for numbers 1 to 10, p stands for numbers 0 to 10, $U^1$ stands $Q^1$ or E, $U^2$ stands $Q^2$ or E with E meaning the group

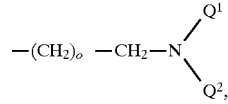

in which o stands for numbers 1 to 6, $Q^1$ stands for a hydrogen atom or $Q^2$ and $Q^2$ stands for a direct bond, M stands for a $C_1$–$C_{10}$ alkylene chain which optionally is interrupted by 1 to 3 oxygen atoms and/or optionally is substituted with 1 to 2 oxo groups, $R^o$ stands for a branched or unbranched $C_1$–$C_{10}$ alkyl radical, a nitro, amino, carboxylic acid group or for

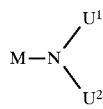

in which number $Q^2$ corresponds to base multiplicity a.

3. Cascade polymer complexes according to claim 1, wherein cascade reproduction units X, Y, Z and W, independently of one another, stand for

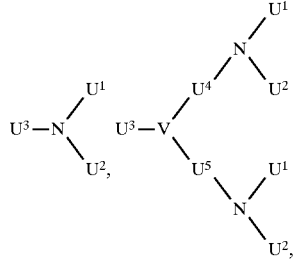

-continued $$\left\{ \begin{array}{c} \overset{U^6}{\underset{|}{N}} \\ U^3-N \quad N-U^6 \\ \underset{|}{N} \\ \underset{U^6}{\underset{|}{N}} \end{array} \right\}_t$$

with t meaning numbers 1 or 2, or $$-CO(CH_2O)_q - \underset{\substack{| \\ L}}{\overset{U^3-N<\overset{U^1}{U^2}}{\bigcirc}} - U^3-N<\overset{U^1}{U^2},$$

in which

U$^1$ stands for Q$^1$ or E,

U$^2$ stands for Q$^2$ or E with E meaning the group $$-(CH_2)_o-CH_2-N\overset{Q^1}{\underset{Q^2}{\diagdown}},$$

in which o stands for numbers 1 to 6,

Q$^1$ stands for a hydrogen atom or Q$^2$,

Q$^2$ stands for a direct bond,

U$^3$ stands for an —NHCO—(CH$_2$)$_o$ chain or a C$_1$–C$_{20}$ alkylene chain, which optionally is interrupted by 1 to 10 oxygen atoms and/or 1 to 2 —N(CO)$_q$—R$^2$ radicals, 1 to 2 phenylene radicals and/or 1 to 2 phenylenoxy radicals and/or optionally is substituted by 1 to 2 oxo, thioxo, carboxy, C$_1$–C$_5$ alkylcarboxy, C$_1$–C$_5$ alkoxy, hydroxy, C$_1$–C$_5$ alkyl groups, in which q stands for numbers 0 or 1 and R$^2$ stands for a hydrogen atom, a methyl or an ethyl radical, which optionally is substituted with 1–2 hydroxy or 1 carboxy group(s), L stands for a hydrogen atom or the group $$U^3-N<\overset{U^1}{U^2},$$

V stands for methine group $$-\underset{|}{\overset{|}{C}H},$$

if at the same time U$^4$ means a direct bond or group M and U$^5$ has one of the meanings of U$^3$ or V stands for group $$-NH-\underset{}{\overset{CO-}{\bigcirc}}-CO-,$$

if at the same time U$^4$ and U$^5$ are identical and mean the direct bond or group M, and U$^6$ stands for group $$-(CO)_q(CH_2)_o-N\overset{Q^1}{\underset{Q^2}{\diagdown}}$$

or a direct bond provided that at least one of the cascade reproduction units stands for the above-indicated 1,4,7,10-tetraazacyclododecane or 1,4,8,11-tetraazacyclotetradecane reproduction unit.

4. Cascade polymer complexes according to claim 1, wherein complexing agent radical K bound to the terminal nitrogen atoms of the last generation of reproduction unit W stands for a radical of general formula IA, IB or IC $$\begin{array}{c} R^1OOC-R^2HC \\ \diagdown \\ N-CH_2-CH_2-N \\ | \quad\quad\quad\quad\quad | \\ CH_2 \quad\quad\quad CH_2 \\ | \quad\quad\quad\quad\quad | \\ CH_2 \quad\quad\quad CH_2 \\ | \quad\quad\quad\quad\quad | \\ N-CH_2-CH_2-N \\ \diagup \quad\quad\quad\quad\quad\quad \diagdown \\ CHR^2-COOR^1 \quad\quad CHR^2-COOR^1 \end{array} \quad (IA)$$

$$\begin{array}{c} \quad\quad\quad\quad\quad\quad R^5 \\ \quad\quad\quad\quad\quad\quad | \\ R^1OOC-H_2C \quad\quad CH-CO-\alpha \quad CH_2-COOR^1 \\ \diagdown \quad\quad\quad\quad | \quad\quad\quad\quad\quad | \\ N-CH_2CH_2-N-CH_2CH_2-N, \\ \diagup \quad\quad\quad\quad\quad\quad\quad\quad\quad | \\ R^1OOC-H_2C \quad\quad\quad\quad\quad\quad CH_2-COOR^1 \end{array} \quad (IB)$$

or $$\begin{array}{c} R^1OOC-H_2C \quad\quad CH_2-COOR^1 \;\; CH_2-CO-\alpha \\ \diagdown \quad\quad\quad\quad\quad | \quad\quad\quad\quad\quad | \\ N-CH_2CH_2-N-CH_2CH_2-N, \\ \diagup \quad\quad\quad\quad\quad\quad\quad\quad | \\ R^1OOC-H_2C \quad\quad\quad\quad\quad\quad CH_2-COOR^1 \end{array} \quad (IC)$$

in which

R$^1$, independently of one another, stand for a hydrogen atom or a metal ion equivalent of atomic numbers 20–29, 39, 42–44 or 57–83, R$^2$ stands for a hydrogen atom, a methyl or an ethyl radical, which optionally is substituted with 1–2 hydroxy or 1 carboxy group(s), R$^3$ stands for a $$\begin{array}{c} R^4 \quad\quad R^2 \\ | \quad\quad\quad | \\ -CH-CO-N-U^2-T \end{array}$$

group or a

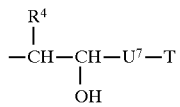

group

R⁴ stands for a hydrogen atom or a straight-chain, branched, saturated or unsaturated $C_1$–$C_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s), R⁵ stands for a hydrogen atom or for R⁴, U⁷ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), and the phenylene groups that are optionally contained can be substituted by 1–2 carboxy, 1–2 sulfo or 1–2 hydroxy groups, T stands for a —CO—α, —NHCO—α or —NHCS—α group and α stands for the bonding site to the terminal nitrogen atoms of the last generation, of reproduction unit W.

5. Cascade polymer complexes according to claim 4, wherein the $C_1$–$C_{20}$ alkylene chain that stands for U⁷ contains the groups —CH₂, —CH₂NHCO, —NHCOCH₂O, —NHCOCH₂OC₆H₄, —N(CH₂CO₂H ), —NHCOCH₂C₆H₄, —NHCSNHC₆H₄, —CH₂OC₆H₄, or —CH₂CH₂O and/or is substituted by groups —COOH, —CH₂COOH.

6. Cascade polymer complexes according to claim 4, wherein U⁷ stands for a

—CCH₂, —CH₂CH₂, —CH₂CH₂CH₂, —C₆H₄,
—C₆H₁₀, —CH₂C₆H₅,
—CH₂NHCOCH₂CH(CH₂CO₂H)—C₆H₄,
—CH₂NHCOCH₂OCH₂, or
—CH₂NHCOCH₂C₆H₄ group.

7. Cascade polymer complexes according to claim 3, wherein radical U³ contained in cascade reproduction units X, Y, Z and W stands for —CO—, —COCH₂OCH₂CO—, —COCH₂—,
—CH₂CH₂—, —CONHC₆H₄—, —NHCOCH₂—,
—COCH₂CH₂CO—, —COCH₂—CH₂CH₂CO—,
—COCH₂CH₂CH₂CH₂CO—,
—CONHCH₂CH₂NHCOCH₂CH₂CO—, or
—COCH₂CH₂NHCOCH₂CH₂CO—, radical U⁴ stands for a direct bond, or for —CH₂CO—, radical U⁵ stands for a direct bond, for —(CH₂)₄—,
—CH₂CO—,
—CH(COOH)—, CH₂OCH₂CH₂—, —CH₂C₆H₄—, or
CH₂—C₆H₄OCH₂CH₂—, radical E stands for a group

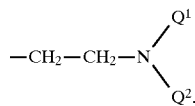

8. Cascade polymer complexes according to claim 3, wherein cascade reproduction units X, Y, Z and W, independently of one another, stand for —CH₂CH₂NH—; —CH₂CH₂N<;
—COCH(NH—)(CH₂)₄NH—; —COCH(N<)(CH₂)₄N<;
—COCH₂OCH₂CON(CH₂CH₂NH—)₂;
—COCH₂OCH₂CON(CH₂CH₂N<)₂;
—COCH₂N(CH₂CH₂NH—)₂; —COCH₂N(CH₂CH₂N<)₂;
—COCH₂NH—; —COCH₂N<;
—COCH₂CH₂CON(CH₂CH₂NH—)₂;
—COCH₂CH₂CON(CH₂CH₂N<)₂;
—COCH₂OCH₂CONH—C₆H₄—CH[CH₂CON(CH₂CH₂NH—)₂]₂;
—COCH₂OCH₂CONH—C₆H₄—CH[CH₂CON(CH₂CH₂N<)₂]₂;
—COCH₂CH₂CO—NH—C₆H₄—CH[CH₂CON(CH₂CH₂NH—)₂]₂;
—COCH₂CH₂CO—NH—C₆H₄—CH[CH₂CON(CH₂CH₂N<)₂]₂;
—CONH—C₆H₄—CH[CH₂CON(CH₂CH₂NH—)₂]₂;
—CONH—C₆H₄—CH[CH₂CON(CH₂CH₂N<)₂]₂;
—COCH(NH—)CH(COOH)NH—; —COCH(N<)CH(COOH)N<;

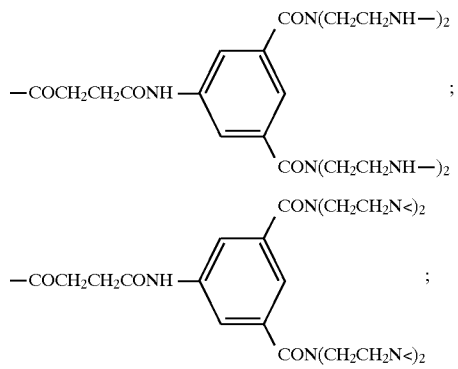

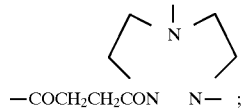

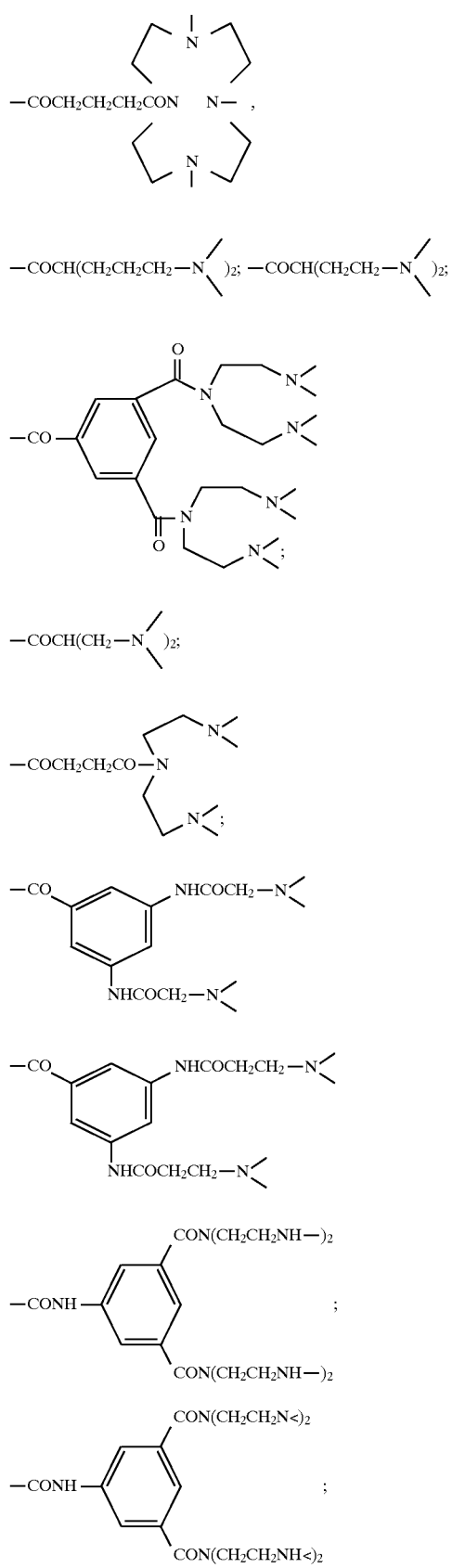
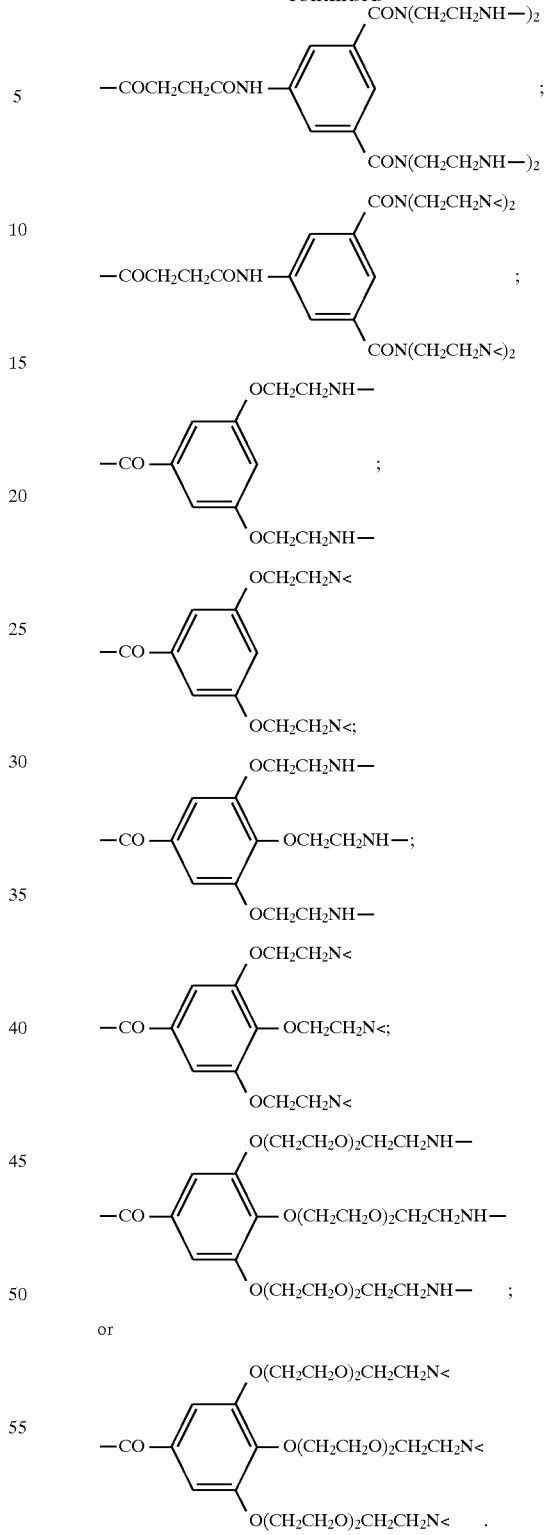
9. Cascade polymer complexes according to claim 2, wherein
m stands for numbers 1–3,
n stands for numbers 1–3,
o stands for number 1,
p stands for numbers 0–3,
M stands for a —CH$_2$, —CO or —CH$_2$CO group and $R^o$ stands for a —$CH_2NU^1U^2$, $CH_3$ or $NO_2$ group.

10. Pharmaceutical agents that contain at least one cascade polymer complex according to claim 1, optionally with the additives usual in galenicals.

11. A method of MRI imaging a patient comprising administering to the patient a complex of claim 1 for differentiating benign and malignant tumors in regions of the patient's body without blood-brain barriers.

12. Process for the production of cascade polymer complexes according to claim 1, wherein compounds of general formula I'

$$A\text{---}\{X\text{---}[Y\text{---}(Z\text{---}\{W\text{---}\beta_W\}_z)_y]_x\}a \qquad (I'),$$

in which

A stands for a nitrogen-containing cascade nucleus of base multiplicity a,

X and Y, independently of one another, stand for a direct bond or a cascade reproduction unit of reproduction multiplicity x or y, Z and W, independently of one another, stand for a cascade reproduction unit of reproduction multiplicity z or w, a stands for numbers 2 to 12, x, y, z and w, independently of one another, stand for numbers 1 to 4 and β stands for the bonding site of the terminal NH groups of the last generation, of reproduction unit W provided that at least two reproduction units are different, that $16 \leq a \cdot x \cdot y \cdot z \cdot w \leq 64$ holds true for the product of multiplicities, and that at least one of cascade reproduction units X, Y, Z, W stands for a 1,4,7,10-tetraazacyclododecane or 1,4,8,11-tetraazacyclotetradecane reproduction unit, are reacted with a complex of complexing agent K' of general formula I'A, I'B or I'C.

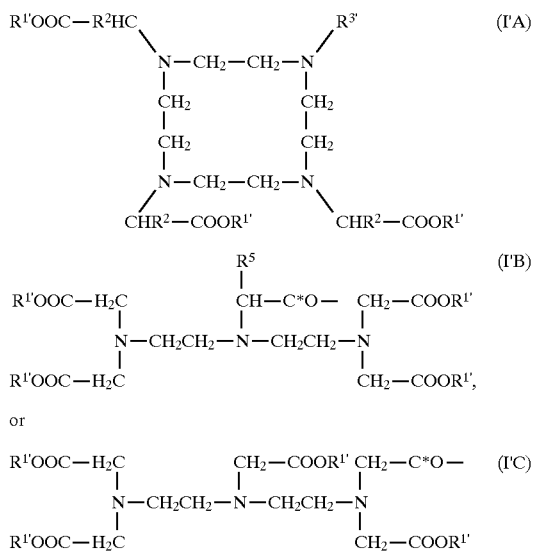

in which

R¹', independently of one another, stand for a hydrogen atom, a metal ion equivalent of atomic numbers 20–29, 39, 42–44, or 57–83 or an acid protective group, R² stands for a hydrogen atom, a methyl or an ethyl radical, which optionally is substituted with 1–2 hydroxy or 1 carboxy group(s), R³' stands for a

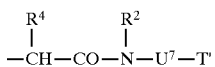

group or a

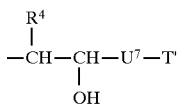

group

R⁴ stands for a hydrogen atom or a straight-chain, branched, saturated or unsaturated $C_1$–$C_{30}$ alkyl chain, which optionally is interrupted by 1–10 oxygen atoms, 1 phenylene group, 1 phenylenoxy group and/or optionally substituted by 1–5 hydroxy, 1–3 carboxy, 1-phenyl group(s), R⁵ stands for a hydrogen atom or for R⁴, U⁷ stands for a straight-chain, branched, saturated or unsaturated $C_1$–$C_{20}$ alkylene group optionally containing 1–5 imino, 1–3 phenylene, 1–3 phenylenoxy, 1–3 phenylenimino, 1–5 amide, 1–2 hydrazide, 1–5 carbonyl, 1–5 ethylenoxy, 1 urea, 1 thiourea, 1–2 carboxyalkylimino, 1–2 ester groups; 1–10 oxygen, 1–5 sulfur and/or 1–5 nitrogen atom(s) and/or optionally substituted by 1–5 hydroxy, 1–2 mercapto, 1–5 oxo, 1–5 thioxo, 1–3 carboxy, 1–5 carboxyalkyl, 1–5 ester and/or 1–3 amino group(s), and the phenylene groups that are optionally contained can be substituted by 1–2 carboxy, 1–2 sulfo or 1–2 hydroxy groups, T' stands for a —C*O, —COOH, —N=C=O or —N=C=S group, and C*O stands for an activated carboxyl group provided that—if K' stands for a complex—at least two (in the case of divalent metals) or three (in the case of trivalent metals) of substituents R¹ stand for a metal ion equivalent of the above-mentioned elements and that optionally other carboxyl groups are present in the form of their salts with inorganic and/or organic bases, amino acids or amino acid amides, optionally present protective groups are cleaved, the thus obtained cascade polymers—if K' stands for a complexing agent —are reacted with at least one metal oxide or metal salt of an element of atomic numbers 20–29, 39, 42, 44, or 57–83 and optionally then in the cascade polymer complexes thus obtained, acid hydrogen atoms that are still present are completely or partially substituted by cations of inorganic and/or organic bases, amino acids, or amino acid amides and optionally still present free terminal amino groups are optionally acylated—before or after the metal complexing.

13. Process for the production of pharmaceutical agents according to claim 10, wherein the cascade polymer complexes, dissolved or suspended in water or physiological salt solution, optionally with the additives usual in galenicals, are brought into a form suitable for enteral or parenteral administration.

* * * * *